US011020061B2

(12) United States Patent
Konno et al.

(10) Patent No.: US 11,020,061 B2
(45) Date of Patent: Jun. 1, 2021

(54) VITAL SIGNS INFORMATION SYNCHRONIZATION SYSTEM, VITAL SIGNS INFORMATION SYNCHRONIZATION METHOD, AND VITAL SIGNS INFORMATION DETECTING SENSOR

(71) Applicant: Nihon Kohden Corporation, Tokyo (JP)

(72) Inventors: Norihito Konno, Tokyo (JP); Yosuke Nagasawa, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 217 days.

(21) Appl. No.: 16/043,609

(22) Filed: Jul. 24, 2018

(65) Prior Publication Data
US 2019/0029607 A1 Jan. 31, 2019

(30) Foreign Application Priority Data
Jul. 25, 2017 (JP) .............................. JP2017-143374

(51) Int. Cl.
*A61B 5/00* (2006.01)
*A61B 5/0205* (2006.01)
(Continued)

(52) U.S. Cl.
CPC .......... *A61B 5/7289* (2013.01); *A61B 5/0006* (2013.01); *A61B 5/0205* (2013.01);
(Continued)

(58) Field of Classification Search
CPC ....... A61B 5/7289; A61B 5/0006; A61B 5/11; A61B 5/0205; A61B 5/0402; A61B 5/02438; A61B 2562/0219; A61B 5/7425
See application file for complete search history.

(56) References Cited

U.S. PATENT DOCUMENTS 6,366,805 B1 * 4/2002 Lutz ..................... A61B 5/0006
600/345
8,421,642 B1 * 4/2013 McIntosh ................ G06F 3/017
340/686.1
(Continued)

FOREIGN PATENT DOCUMENTS

JP 2013-027044 A 2/2013
JP 2014-068718 A 4/2014
(Continued)

OTHER PUBLICATIONS

Japan Office Action dated Mar. 16, 2021 issued in Japanese Patent Application No. 2017-143374.

*Primary Examiner* — Gary Jackson
*Assistant Examiner* — Sebastian X Lukjan
(74) *Attorney, Agent, or Firm* — Pearne & Gordon LLP

(57) ABSTRACT

A first vital signs information detecting sensor and a second vital signs information sensor are attached to a living body. The first vital signs information detecting sensor detects over time first vital signs information and first motion information of the living body. The first vital signs information and the first motion information are transmitted from the first vital signs information detecting sensor to a receiver. The second vital signs information detecting sensor detects over time second vital signs information and second motion information of the living body. The second vital signs information and the second motion information are transmitted from the second vital signs information detecting sensor to the receiver. The first vital signs information and the second vital signs information are displayed on a display of the receiver in a synchronized state, on the basis of the first motion information and the second motion information.

3 Claims, 29 Drawing Sheets

(51) Int. Cl.
*A61B 5/11* (2006.01)
*A61B 5/024* (2006.01)
*A61B 5/318* (2021.01)

(52) U.S. Cl.
CPC ............. *A61B 5/11* (2013.01); *A61B 5/02438* (2013.01); *A61B 5/318* (2021.01); *A61B 5/7425* (2013.01); *A61B 2562/0219* (2013.01)

(56) References Cited

U.S. PATENT DOCUMENTS

| | | | |
|---|---|---|---|
| 2009/0082635 A1* | 3/2009 | Baldus | A61B 5/0002 600/300 |
| 2013/0023746 A1 | 1/2013 | Kilim et al. | |
| 2014/0039289 A1 | 2/2014 | Kilim et al. | |
| 2016/0255600 A1 | 9/2016 | Hayami et al. | |
| 2018/0055382 A1* | 3/2018 | Woodward | A61B 5/0024 |

FOREIGN PATENT DOCUMENTS

| | | | | |
|---|---|---|---|---|
| JP | 2015-093125 A | 5/2015 | | |
| JP | 2016-054888 A | 4/2016 | | |
| WO | WO-2018004614 A1 * | 1/2018 | ........... | A61B 5/0017 |

* cited by examiner

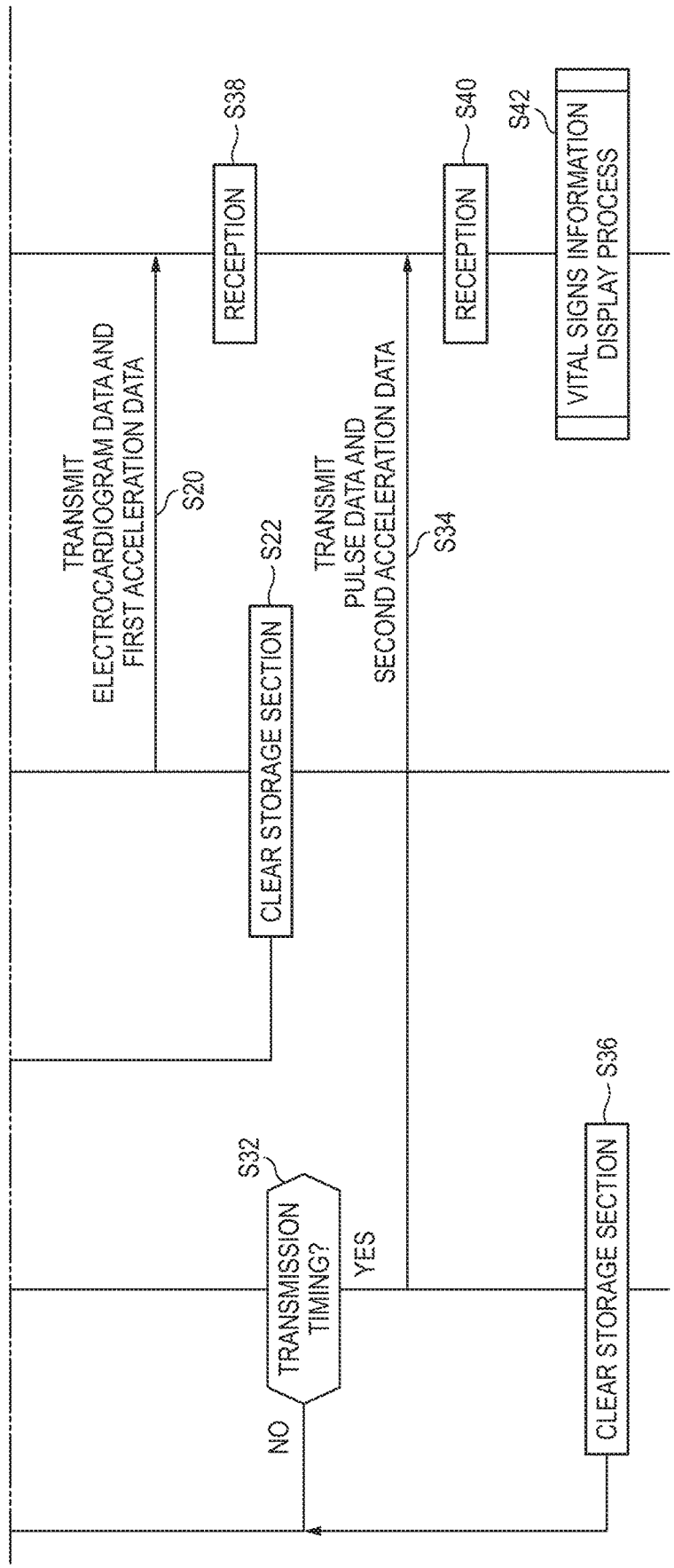

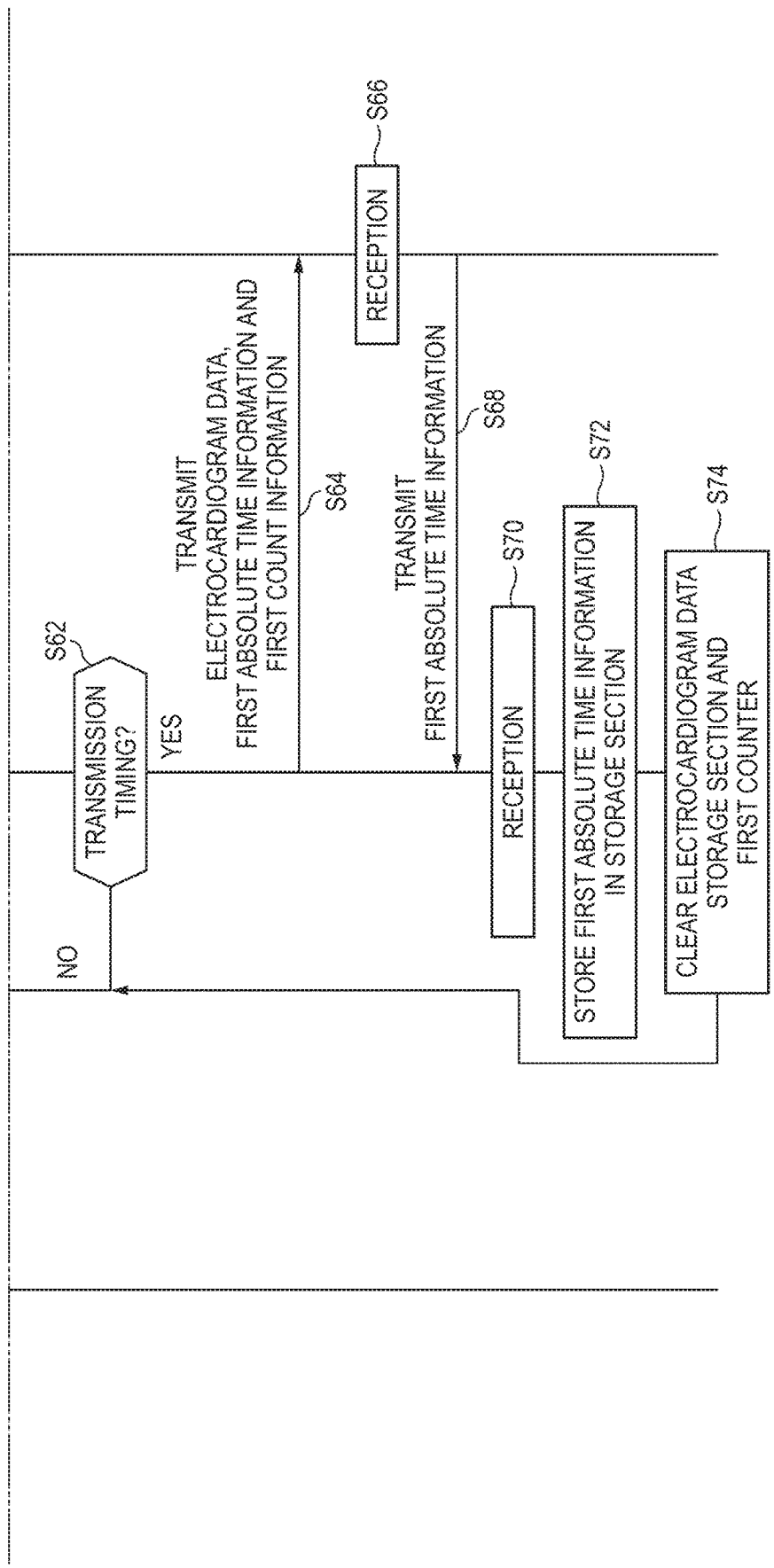

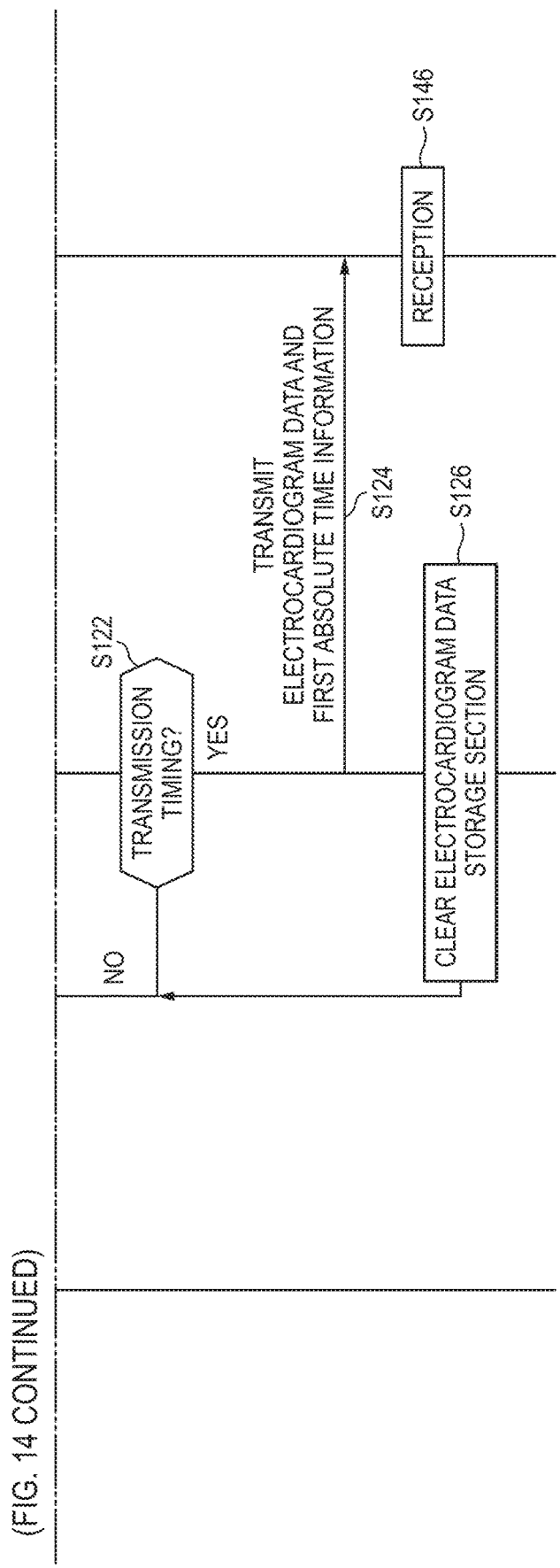

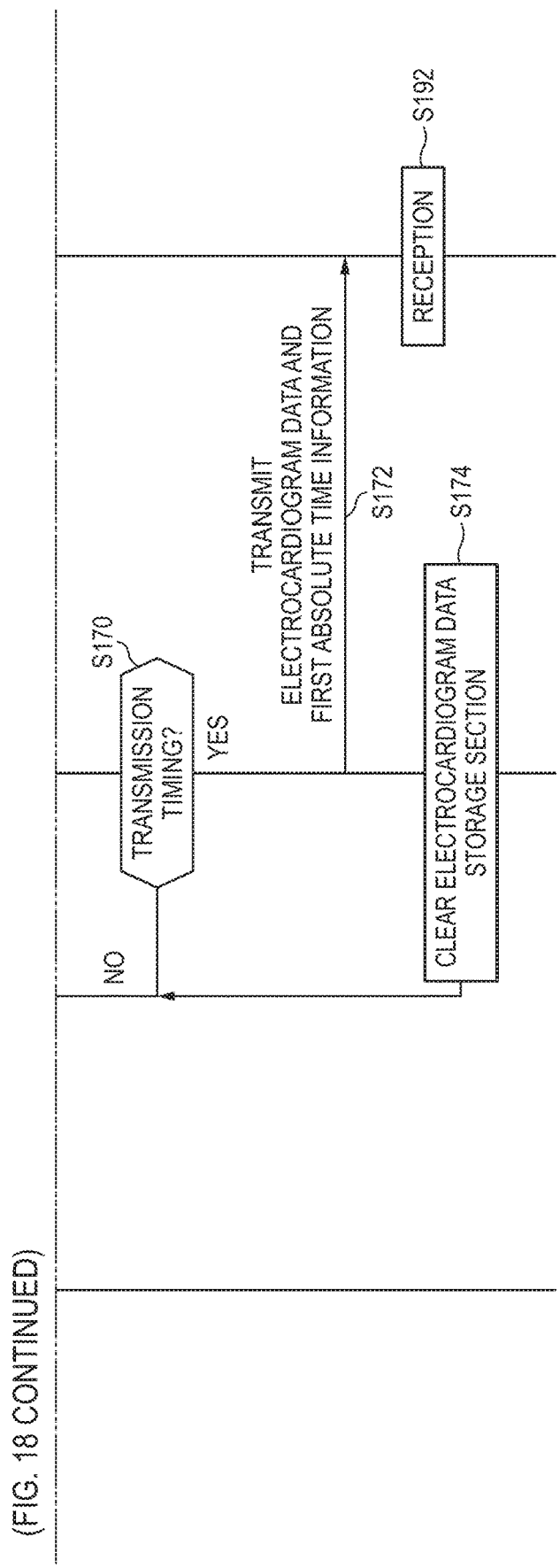
(FIG. 18 CONTINUED)

VITAL SIGNS INFORMATION SYNCHRONIZATION SYSTEM, VITAL SIGNS INFORMATION SYNCHRONIZATION METHOD, AND VITAL SIGNS INFORMATION DETECTING SENSOR

CROSS-REFERENCE TO RELATED APPLICATION(S)

This application is based upon and claims the benefit of priority from prior Japanese patent application No. 2017-143374, filed on Jul. 25, 2017, the entire contents of which are incorporated herein by reference.

BACKGROUND

1. Technical Field

The present disclosure relates to a vital signs information synchronization system, a vital signs information synchronization method, and a vital signs information detecting sensor.

2. Background Art

A vital signs information detecting sensor equipped with a wireless communication section (a medical telemeter) is known in the field of medical devices. For example, Japanese Patent Publication No. 2014-068718A discloses such a sensor.

In the case where a plurality of vital signs information detecting sensors such as an electrocardiogram detecting sensor and a pulse detecting sensor are used while attached to the same living body, however, the vital signs information detecting sensors wirelessly transmit at different timings sets of vital signs information (for example, electrocardiogram data and pulse data) which are detected respectively by the sensors. Therefore, even if sets of vital signs information are detected at the same time, it is impossible for the receiving side of the vital signs information to recognize the vital signs information which is detected by each of the vital signs information detecting sensors as the sets of vital signs information which are detected at the same time. As a result, for example, electrocardiogram data and pulse data cannot be displayed in a state where the two kinds of data are synchronized.

It is an object of the present disclosure to provide a vital signs information synchronization system, a vital signs information synchronization method, and a vital signs information detecting sensor which, even when a plurality of vital signs information detecting sensors wirelessly transmit at different timings sets of vital signs information (for example, electrocardiogram data and pulse data) that are detected respectively by the sensors, enable the receiving side of the vital signs information to treat the vital signs information (for example, electrocardiogram data and pulse data) as sets of vital signs information that are detected at the same time, so that, for example, the electrocardiogram data and the pulse data can be displayed in a state where the two kinds of data are synchronized.

SUMMARY

In order to achieve the above object, according to one aspect of the present disclosure, there is provided a vital signs information synchronization system comprising: a first vital signs information detecting sensor; a second vital signs information detecting sensor; and an information processing device, wherein the first vital signs information detecting sensor and the second vital signs information detecting sensor are configured to be attached on a living body; wherein the first vital signs information detecting sensor comprises: a first vital signs information detecting section configured to detect over time first vital signs information of the living body; a first motion detecting section configured to detect over time first motion information of the living body; and a first transmitting section configured to transmit to the information processing device the first vital signs information detected by the first vital signs information detecting section and the first motion information detected by the first motion detecting section; wherein the second vital signs information detecting sensor comprises: a second vital signs information detecting section configured to detect over time second vital signs information of the living body; a second motion detecting section configured to detect over time second motion information of the living body; and a second transmitting section configured to transmit to the information processing device the second vital signs information detected by the second vital signs information detecting section and the second motion information detected by the second motion detecting section; and wherein the information processing device comprises: a receiving section configured to receive the first vital signs information and the first motion information transmitted by the first transmitting section as well as the second vital signs information and the second motion information transmitted by the second transmitting section; a display; and a display control section configured to cause the display to display the first vital signs information and the second vital signs information received by the receiving section in a synchronized state, on the basis of the first motion information and the second motion information received by the receiving section.

According to the above configuration, even when the first and second vital signs information detecting sensors wirelessly transmit at different timings the sets of vital signs information (for example, electrocardiogram data and pulse data) which are detected respectively by the sensors, the information processing device, which is the receiving side of the vital signs information, can treat the sets of vital signs information as if they are detected respectively by the first and second vital signs information detecting sensors at the same time.

This is because, the information processing device (receiver) causes the first vital signs information and the second vital signs information to be displayed on the display in a synchronized state based on the first motion information (for example, first acceleration data) and the second motion information (for example, second acceleration data) which are received by the information processing device.

DETAILED DESCRIPTION OF EXEMPLARY EMBODIMENTS

First Embodiment

Figure 1:
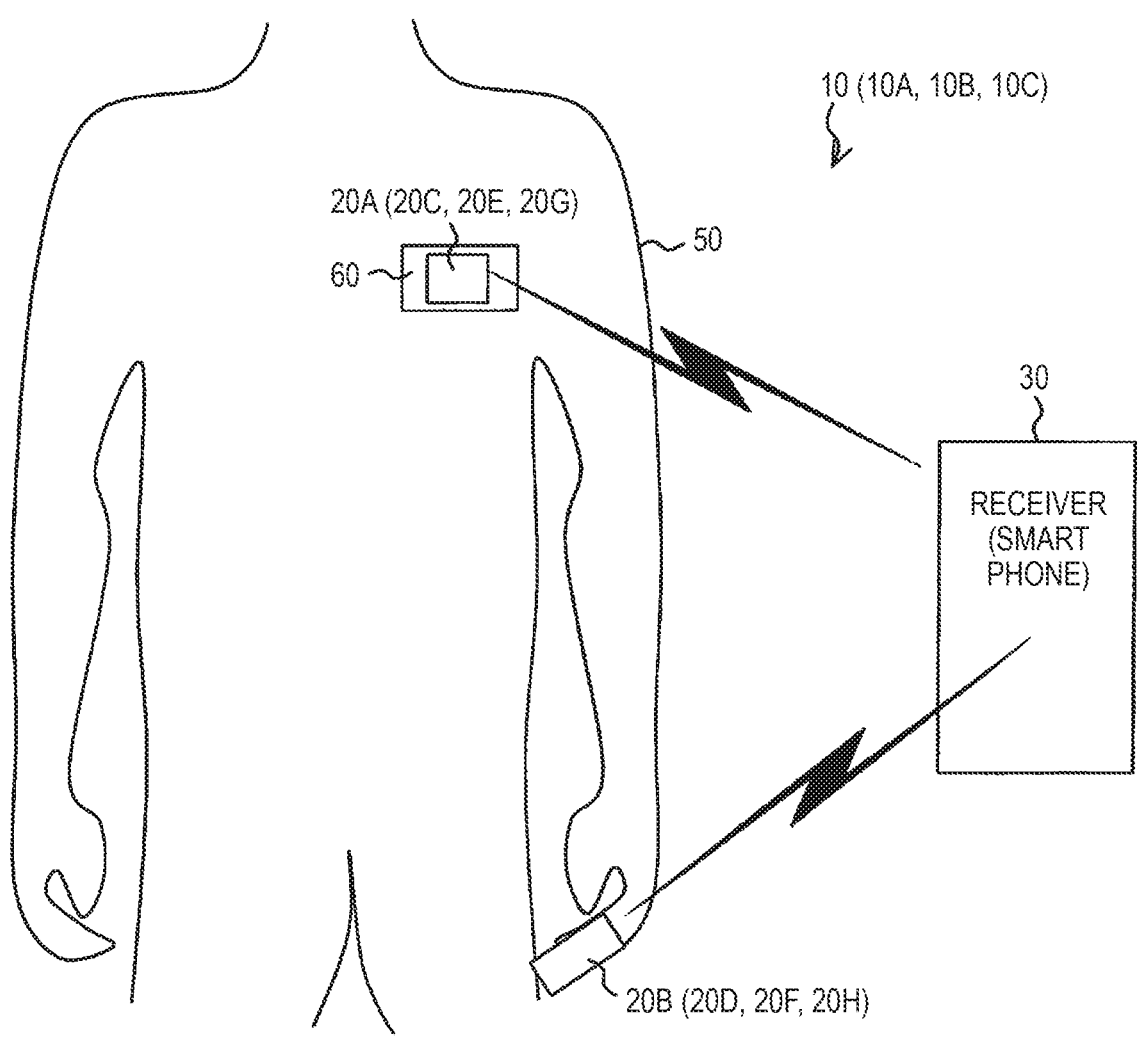
FIG. 1 is a schematic diagram of a medical telemetry system.

Hereinafter, a medical telemetry system 10 which is a first embodiment of the present disclosure will be described with reference to the accompanying drawings. In the drawings, components which correspond to each other are denoted by the same reference numerals or symbols. Duplicative description for such components will be omitted.

FIG. 1 is a schematic diagram of the medical telemetry system 10.

As illustrated in FIG. 1, a vital signs information synchronization system (hereinafter, referred to as the medical telemetry system 10) includes a first vital signs information detecting sensor 20A, a second vital signs information detecting sensor 20B, an information processing device (hereinafter, referred to as a receiver 30), etc. In the case where the first vital signs information detecting sensor 20A and the second vital signs information detecting sensor 20B are not particularly distinguished from each other, the sensors will be hereinafter referred to as the vital signs information detecting sensor 20.

[First Vital Signs Information Detection Sensor]

Figure 2A:
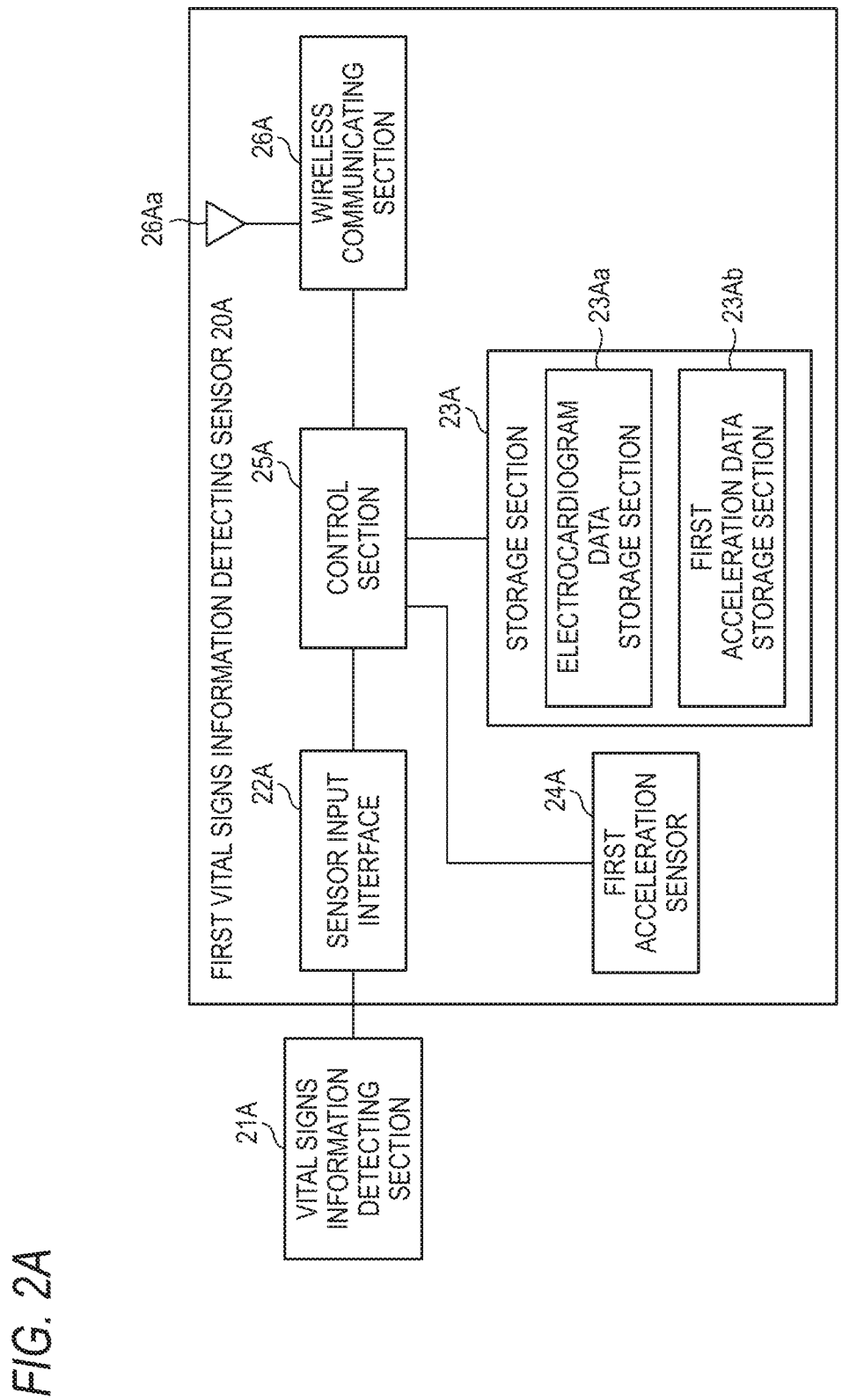
FIG. 2A is a schematic hardware diagram of a first vital signs information detecting sensor in the medical telemetry system of the first embodiment.

Next, the first vital signs information detecting sensor 20A will be described. FIG. 2A is a schematic hardware diagram of the first vital signs information detecting sensor 20A.

As illustrated in FIG. 2A, the first vital signs information detecting sensor 20A includes a vital signs information detecting section 21A, a sensor input interface 22A, a storage section 23A, a first acceleration sensor 24A, a control section 25A, and a wireless communicating section 26A.

As illustrated in FIG. 1, the vital signs information detecting sensor 20A is attached to a pad 60 which is pasted to a living body (hereinafter, referred to as the patient 50), measures vital signs information (here, an electrocardiogram) of the patient 50, and wirelessly transmits the measured vital signs information through the wireless communicating section 26A to the receiver 30 and the like.

As illustrated in FIG. 2A, vital signs information detecting section 21A is configured by three lead electrodes (R, L, F) which detect over time an electrocardiogram of the patient 50 as vital signs information (or a vital signs signal) of the patient 50.

Figure 6A:
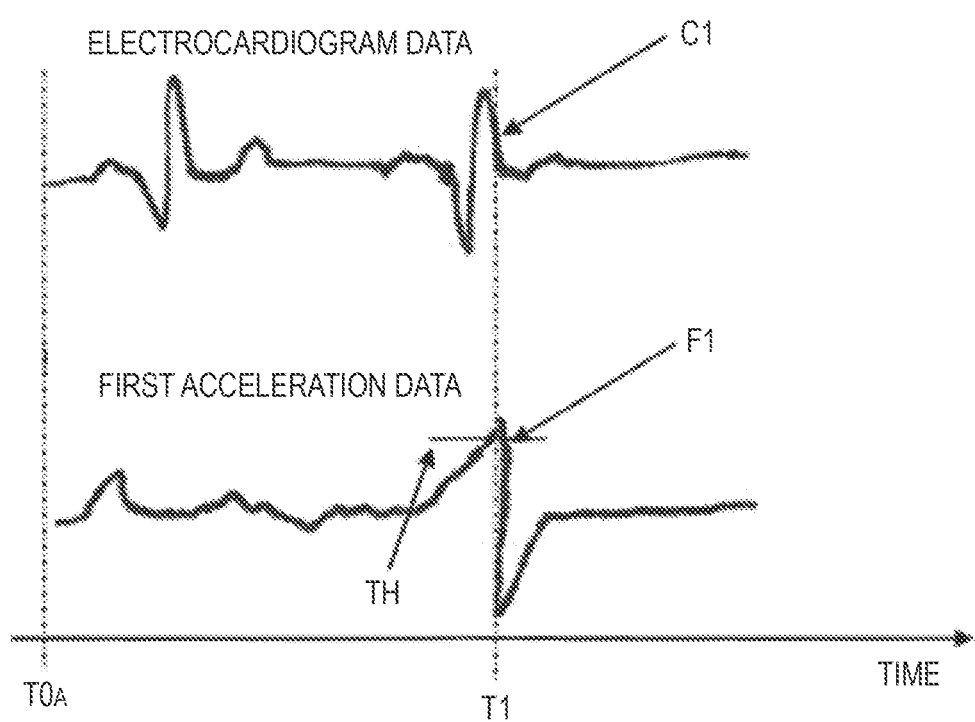
FIG. 6A illustrates examples of electrocardiogram data and first acceleration data.

The sensor input interface 22A applies amplification, A/D conversion, and the like on the vital signs information of the patient 50 which is detected by the vital signs information detecting section 21A, and then supplies the resulting data to the control section 25A. Specifically, the sensor input interface 22A supplies to the control section 25A electrocardiogram data configured by a group of data which are sampled at a predetermined sampling frequency (for example, 500 Hz) as vital signs information. The control section 25A causes the electrocardiogram data which are supplied from the sensor input interface 22A, to be stored in an electrocardiogram data storage section 23Aa. FIG. 6A illustrates an example of the electrocardiogram data (a waveform based on the electrocardiogram data) to be stored in the electrocardiogram data storage section 23Aa.

For example, the storage section 23A is a rewritable non-volatile memory such as a flash ROM. The storage section 23A includes the electrocardiogram data storage section 23Aa and a first acceleration data storage section 23Ab. Although not shown, the storage section 23A further stores a control program (firmware).

For example, the first acceleration sensor 24A is a three-axis acceleration sensor (MEMS sensor). The first acceleration sensor 24A is an example of the first motion detecting section. The first acceleration sensor 24A detects (outputs) over time acceleration information of the patient 50. Specifically, the first acceleration sensor 24A outputs as acceleration information (motion information), acceleration data (hereinafter, referred to as the first acceleration data) configured by a group of data which are sampled at a predetermined sampling frequency (for example, 500 Hz). The control section 25A acquires the first acceleration data which are output from the first acceleration sensor 24A, and causes the acquired first acceleration data to be stored in the first acceleration data storage section 23Ab. FIG. 6A illustrates an example of the first acceleration data (a waveform based on the first acceleration data) to be stored in the first acceleration data storage section 23Ab.

The control section 25A includes a CPU and a RAM. The CPU of the first vital signs information detecting sensor 20A controls the wireless communicating section 26A and the like, by executing the control program stored in the storage section 23A. For example, the control section 25A transmits the vital signs information (electrocardiogram data) which is detected by the vital signs information detecting section 21A, and the acceleration information (first acceleration data) which is detected by the first acceleration sensor 24A, to the receiver 30 through the wireless communicating section 26A.

For example, the wireless communicating section 26A is a communication module (e.g., a BLE module) compatible to the BLE (Bluetooth Low Energy) technology, and wirelessly communicates with another BLE compatible device (e.g., the receiver 30) in a short range (e.g., 100 mm) through an antenna 26Aa. The wireless communicating section 26A is an example of the first transmitting section. The first vital signs information detecting sensor 20A serves as a peripheral (referred to also as a slave).

[Second Vital Signs Information Detection Sensor]

Figure 2B:
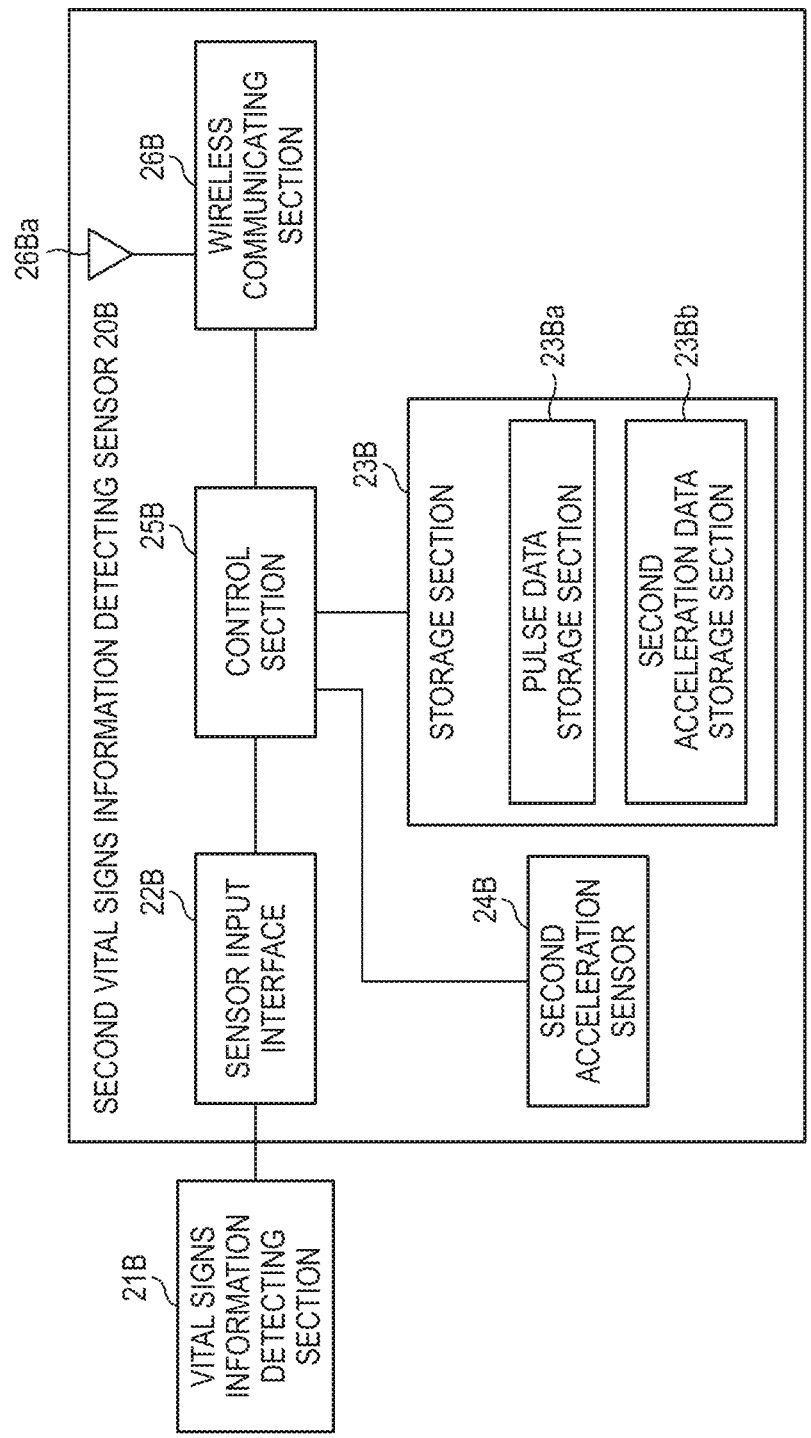
FIG. 2B is a schematic hardware diagram of a second vital signs information detecting sensor in the medical telemetry system of the first embodiment.

Next, the second vital signs information detecting sensor 20B will be described. FIG. 2B is a schematic hardware diagram of the second vital signs information detecting sensor 20B.

As illustrated in FIG. 2B, the second signs information detecting sensor 20B includes a vital signs information detecting section 21B, a sensor input interface 22B, a storage section 23B, a second acceleration sensor 24B, a control section 25B, and a wireless communicating section 26B.

As illustrated in FIG. 1, the second vital signs information detecting sensor 20B is attached to the patient 50, measures vital signs information (here, the pulse) of the patient 50, and transmits the measured vital signs information through the wireless communicating section 26B to the receiver 30 and the like.

As illustrated in FIG. 2B, vital signs information detecting section 21B is configured by an SpO2 probe which detects over time the pulse of the patient 50 as vital signs information (or a vital signs signal) of the patient 50.

Figure 6B:
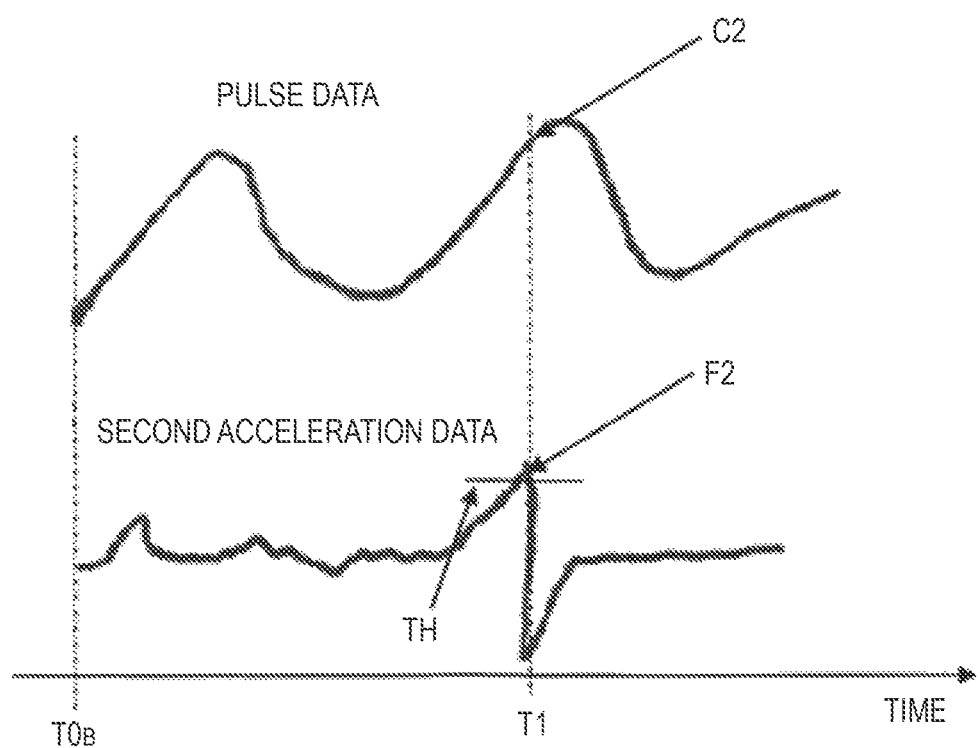
FIG. 6B illustrates examples of pulse data and second acceleration data.

The sensor input interface 22B applies amplification, A/D conversion, and the like on the vital signs information of the patient 50 which is detected by the vital signs information detecting section 21B, and then supplies the resulting data to the control section 25B. Specifically, the sensor input interface 22B supplies to the control section 25B pulse data configured by a group of data which are sampled at a predetermined sampling frequency (for example, 500 Hz), as vital signs information. The control section 25B causes the pulse data which are supplied from the sensor input interface 22B, to be stored in a pulse data storage section 23Ba. FIG. 6B illustrates an example of the pulse data (a waveform based on the pulse data) to be stored in the pulse data storage section 23Ba.

For example, the storage section 23B is a rewritable non-volatile memory such as a flash ROM. The storage section 23B includes the pulse data storage section 23Ba and a second acceleration data storage section 23Bb. Although not shown, the storage section 23B further stores a control program (firmware).

For example, the second acceleration sensor 24B is a three-axis acceleration sensor (MEMS sensor). The second acceleration sensor 24B is an example of the second motion detecting section. The second acceleration sensor 24B detects (outputs) over time acceleration information of the patient 50. Specifically, the second acceleration sensor 24B outputs as acceleration information (motion information), acceleration data (hereinafter, referred to as the second acceleration data) configured by a group of data which are sampled at a predetermined sampling frequency (for example, 500 Hz). The control section 25B acquires the second acceleration data which are output from the second acceleration sensor 24B, and causes the acquired second acceleration data to be stored in the second acceleration data storage section 23Bb. FIG. 6B illustrates an example of the second acceleration data (a waveform based on the second acceleration data) to be stored in the second acceleration data storage section 23Bb.

The control section 25B includes a CPU and a RAM. The CPU of the second vital signs information detecting sensor 20B controls the wireless communicating section 26B and the like, by executing the control program stored in the storage section 23B. For example, the control section transmits the vital signs information (pulse data) which is detected by the vital signs information detecting section 21B, and the acceleration information (second acceleration data) which is detected by the second acceleration sensor 24B, to the receiver 30 through the wireless communicating section 26B.

For example, the wireless communicating section 26B is a communication module (e.g., a BLE module) compatible to the BLE (Bluetooth Low Energy) technology, and wirelessly communicates with another BLE compatible device (e.g., the receiver 30) in a short range (e.g., 100 mm) through an antenna 26Ba. The wireless communicating section 26B is an example of the second transmitting section. The second vital signs information detecting sensor 20B serves as a peripheral (referred to also as a slave).

[Receiver]

Figure 3:
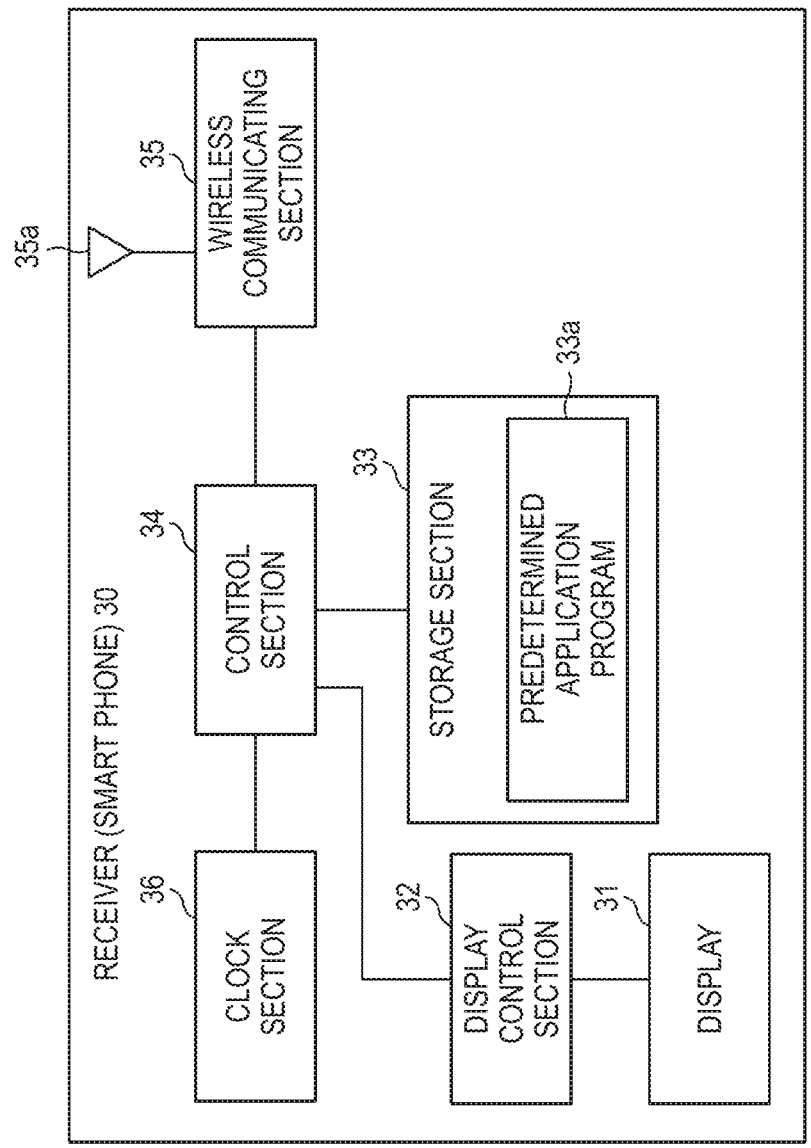
FIG. 3 is a schematic hardware diagram of a receiver in the medical telemetry system of the first embodiment.

Next, the receiver 30 will be described. FIG. 3 is a schematic hardware diagram of the receiver 30.

For example, the receiver 30 is a smart phone, and, as illustrated in FIG. 3, includes a display 31, a display control section 32, a storage section 33, a control section 34, a wireless communicating section 35, and a clock section 36.

For example, the display 31 is a liquid crystal display equipped with a touch panel.

The display control section 32 displays various items on the display 31 under the control of the control section 34. Based on the first acceleration data and the second acceleration data, for example, the display control section 32 displays the electrocardiogram data (specifically, the waveform based on the electrocardiogram data) and the pulse data (specifically, the waveform based on the pulse data) on the display 31 in a state where the two kinds of data are synchronized with each other.

For example, the storage section 33 is a rewritable non-volatile memory such as a flash ROM. The storage section 33 stores a predetermined application program 33a and the like.

The control section 34 includes a CPU and a ROM. The CPU of the receiver 30 controls the display control section 32, the wireless communicating section 35, and the like, by executing the predetermined application program 33a stored in the storage section 33.

For example, the wireless communicating section 35 is a communication module (e.g., a BLE module) compatible to the BLE (Bluetooth Low Energy) technology, and wirelessly communicates with another BLE compatible device (e.g., the vital signs information detecting sensor 20) in a short range (e.g., 100 mm) through an antenna 35a. The wireless communicating section 35 is an example of the receiving section. The receiver 30 serves as a central (also referred to as a master).

The clock section 36 is a clock incorporated in the receiver 30, and, for example, a real-time clock.

[Operation Example of Medical Telemetry System 10]

Figure 4:
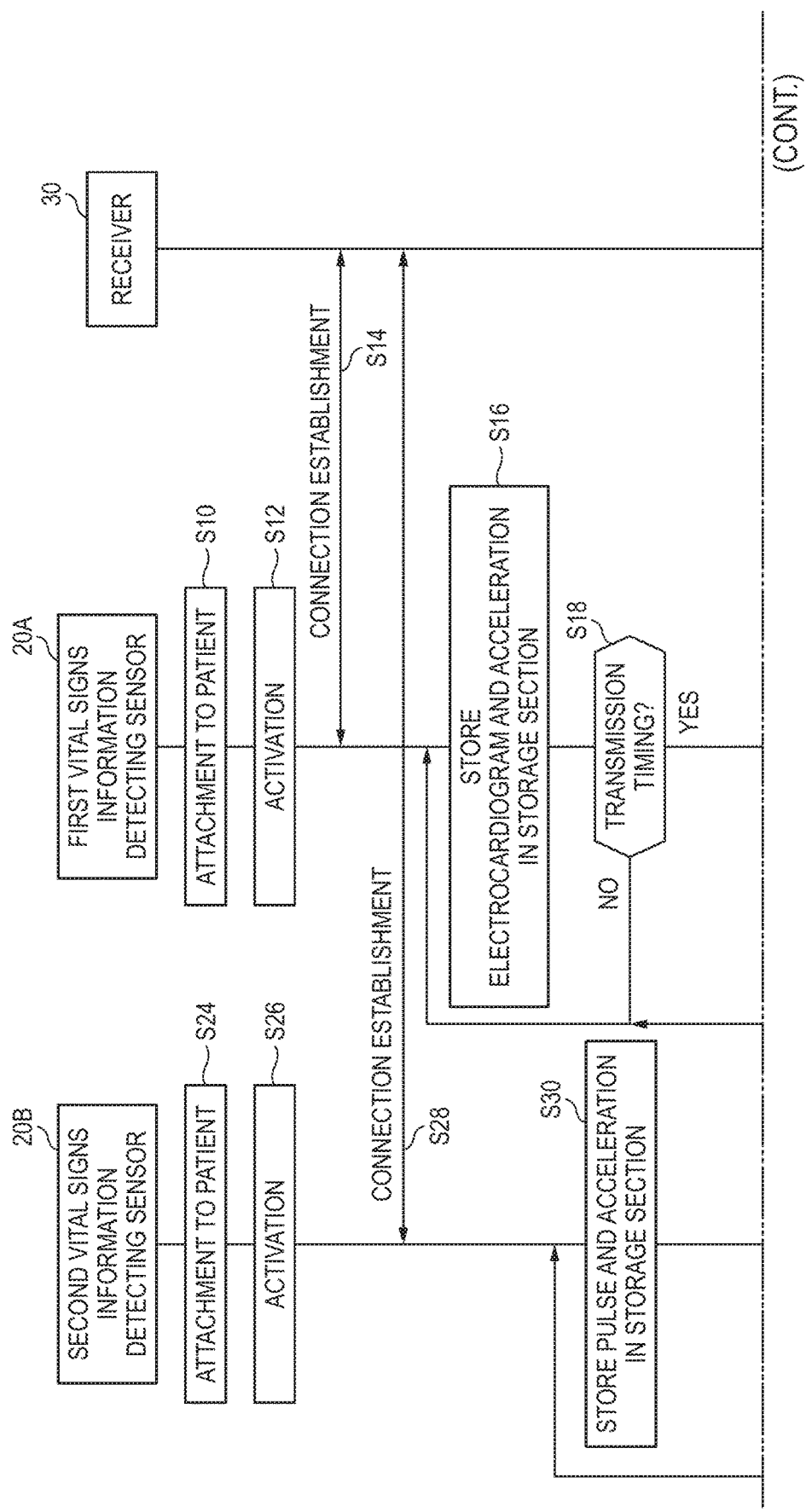
FIG. 4 is a sequence diagram illustrating the operation of the medical telemetry system of the first embodiment.

Next, an operation example of the thus configured medical telemetry system 10 will be described. FIG. 4 is a sequence diagram illustrating the operation of the medical telemetry system 10.

The following process of the receiver 30 is mainly implemented by the CPU of the receiver 30 with the execution of the predetermined application program 33a read from the storage section 33 into the RAM. Moreover, the following process of the vital signs information detecting sensor 20 is mainly implemented by the CPU of the vital signs information detecting sensor 20 with the execution of the control program read from the storage section 23A or 23B into the RAM.

First, the first vital signs information detecting sensor 20A is attached to the patient 50 as illustrated in FIG. 1 (step S10).

Next, when the first vital signs information detecting sensor 20A is activated with an unillustrated power switch (step S12), the first vital signs information detecting sensor 20A communicates according to a standard (the BLE communication standard, the same applies hereinafter), with the receiver 30, thereby establishing a connection (step S14). The CPU of the first vital signs information detecting sensor 20A then causes the electrocardiogram data of the patient 50 which are detected by the vital signs information detecting section 21A, to be stored in the electrocardiogram data storage section 23Aa, and the first acceleration data detected by the first acceleration sensor 24A to be stored in the first acceleration data storage section 23Ab (step S16). In this case, as illustrated in FIG. 6A, the storing of the electrocardiogram data and the first acceleration data is started at the same time $T0_A$ (or a substantially same time $T0_A$). In this way, the electrocardiogram data and the first acceleration data are stored in a synchronized state.

When a transmission timing comes (step S18: Yes), then, the CPU of the first vital signs information detecting sensor 20A reads out the electrocardiogram data and the first acceleration data from the storage section 23A, and transmits the electrocardiogram data and first acceleration data which are read out, to the receiver 30 through the wireless communicating section 26A (step S20). When the wireless communicating section 26A is set to a sleep state until the transmission timing comes, it is possible to save power consumption.

For example, the transmission timing is a timing when the electrocardiogram data (or the first acceleration data) stored in the storage section 23A exceed a threshold.

Alternatively, steps S16 and S18 may be omitted, and the electrocardiogram data of the patient 50 which are detected by the vital signs information detecting section 21A, and the first acceleration data which are detected by the first acceleration sensor 24A may be transmitted directly (without being stored in the storage section 23A) to the receiver 30.

Next, the CPU of the first vital signs information detecting sensor 20A clears the storage section 23A (step S22). Namely, the stored contents in the electrocardiogram data storage section 23Aa and the first acceleration data storage section 23Ab are deleted.

Hereinafter, the first vital signs information detecting sensor 20A repeatedly executes the processes of steps S16 to S22.

Similarly, the second vital signs information detecting sensor 20B is attached to the patient 50 as illustrated in FIG. 1 (step S24).

Next, when the second vital signs information detecting sensor 20B is activated with an unillustrated power switch (step S26), the second vital signs information detecting sensor 20B communicates with the receiver 30 according to the standard, thereby establishing a connection (step S28). Together with this, the CPU of the second vital signs information detecting sensor 20B causes the pulse data of the patient 50 which are detected by the vital signs information detecting section 21B, to be stored in the pulse data storage section 23Ba, and the second acceleration data detected by the second acceleration sensor 24B to be stored in the second acceleration data storage section 23Bb (step S30). In this case, as illustrated in FIG. 6B, the storing of the pulse data and the second acceleration data is started at the same time $T0_B$ (or a substantially same time $T0_B$). In this way, the pulse data and the second acceleration data are stored in a synchronized state. Usually, the time $T0_A$ and the time $T0_B$ are different from each other.

When a transmission timing comes (step S32: Yes), the CPU of the second vital signs information detecting sensor 20B reads out the pulse data and the second acceleration data from the storage section 23B, and transmits the pulse data and second acceleration data which are read out, to the receiver 30 through the wireless communicating section 26B (step S34). When the wireless communicating section 26B is set to a sleep state until the transmission timing comes, it is possible to save power consumption.

For example, the transmission timing is a timing when the pulse data (or the second acceleration data) stored in the storage section 23B exceed a threshold.

Alternatively, steps S30 and S32 may be omitted, and the pulse data of the patient 50 which are detected by the vital signs information detecting section 21B, and the second acceleration data which are detected by the second acceleration sensor 24B may be transmitted directly (without being stored in the storage section 23B) to the receiver 30.

Next, the CPU of the second vital signs information detecting sensor 20B clears the storage section 23B (step S36). Namely, the stored contents of the pulse data storage section 23Ba and the second acceleration data storage section 23Bb are deleted.

Hereinafter, the second vital signs information detecting sensor 20B repeatedly executes the processes of steps S30 to S36.

When the wireless communicating section 35 receives the electrocardiogram data and first acceleration data which are transmitted by the first vital signs information detecting sensor 20A, and the pulse data and second acceleration data which are transmitted by the second vital signs information detecting sensor 20B (steps S38, S40), the receiver 30 executes a vital signs information display process (step S42).

Figure 5:
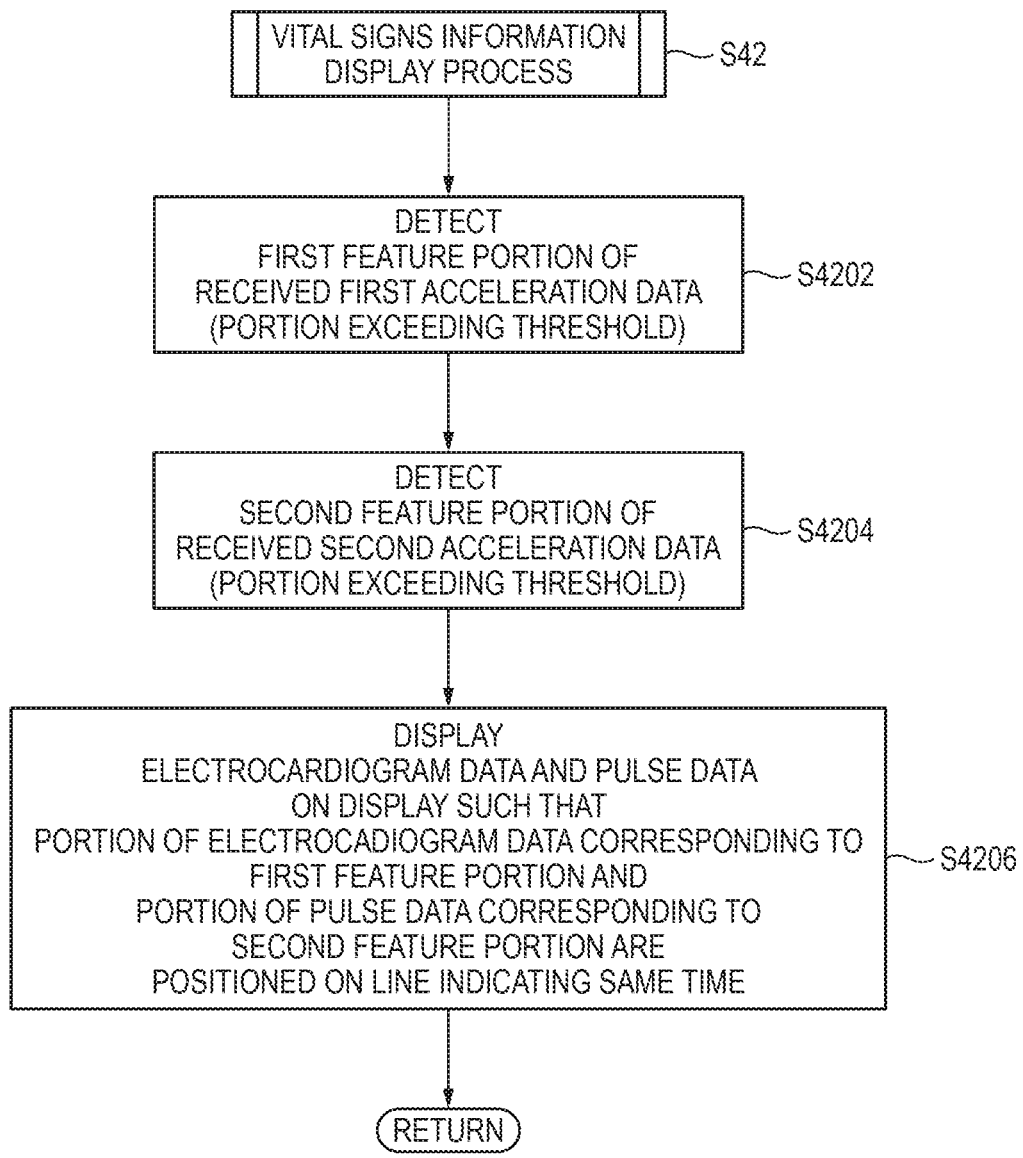
FIG. 5 is a flowchart illustrating a vital signs information display process of the first embodiment.
Figure 7:
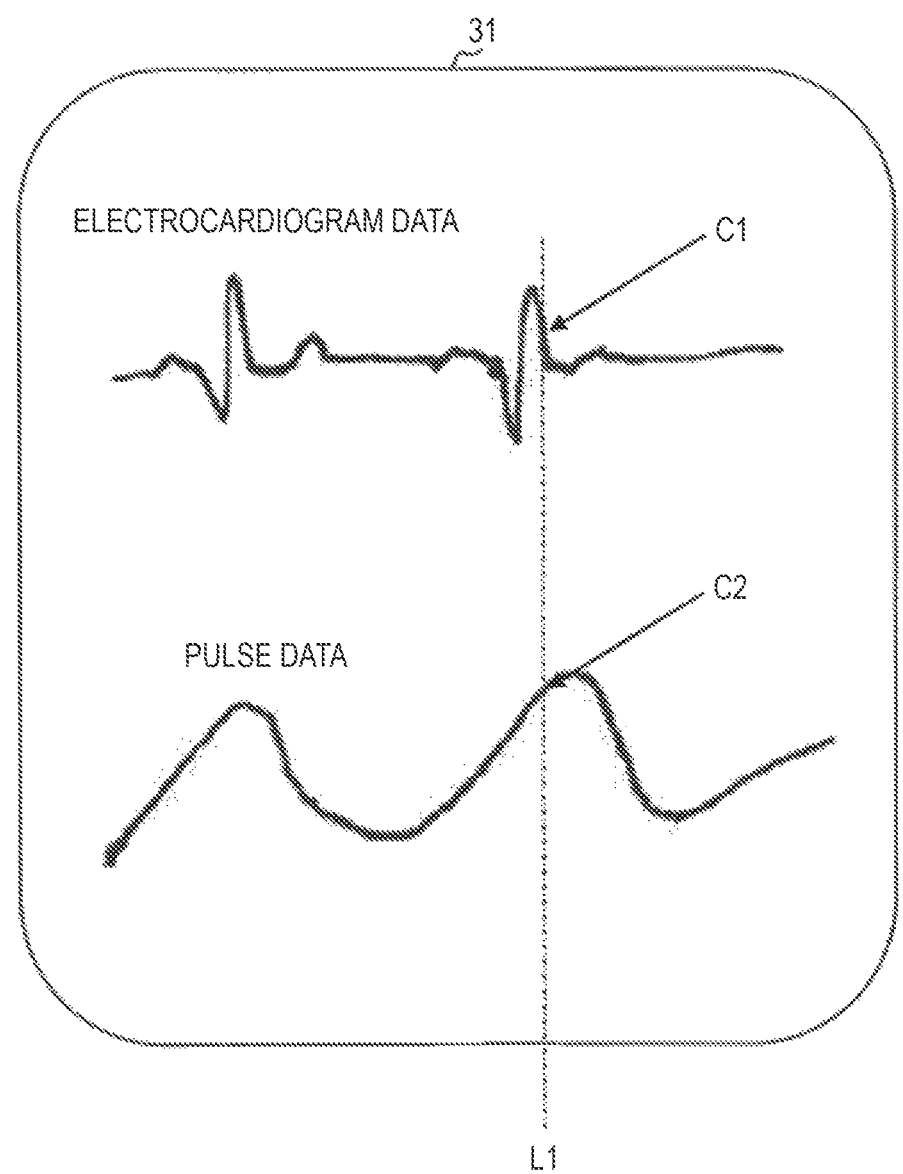
FIG. 7 illustrates display examples of the electrocardiogram data and the pulse data according to the first embodiment.

FIG. 5 is a flowchart illustrating the vital signs information display process. FIG. 6A illustrates examples of the electrocardiogram data and the first acceleration data. FIG. 6B illustrates examples of the pulse data and the second acceleration data. FIG. 7 illustrates display examples of the electrocardiogram data and the pulse data.

The vital signs information display process is a process in which the receiver 30 causes the electrocardiogram data and the pulse data to be displayed on the display 31 in a synchronized state.

Specifically, the CPU of the receiver 30 first detects a first feature portion F1 in the first acceleration data which are received in step S38 (step S4202). As illustrated in FIG. 6A, for example, the first feature portion F1 is a portion which exceeds a threshold TH.

Next, the CPU of the receiver 30 detects a second feature portion F2 in the second acceleration data which are received in step S40 (step S4204). As illustrated in FIG. 6B, for example, the second feature portion F2 is a portion which exceeds the threshold TH.

When it is assumed that the first vital signs information detecting sensor 20A (the first acceleration sensor 24A) and the second vital signs information detecting sensor 20B (the second acceleration sensor 24B) detect the same motion because the sensors are attached to the same patient 50, it can be considered that the first feature portion F1 and the second feature portion F2 are detected at the same time T1.

Therefore, the CPU of the receiver 30 causes the electrocardiogram data and the pulse data to be displayed on the display 31 so that, as illustrated in FIG. 7, a portion C1 (see FIG. 6A) of the electrocardiogram data corresponding to the first feature portion F1, and a portion C2 (see FIG. 6B) of the pulse data corresponding to the second feature portion F2 are positioned on a line L1 indicating the same time (step S4206). Namely, the electrocardiogram data and the pulse data are displayed on the display 31 in a synchronized state. The line L1 may be displayed on the display 31, or may not be displayed.

As has been described above, according to the present embodiment, even when the first and second vital signs information detecting sensors 20A, 20B wirelessly transmit at different timings the sets of vital signs information (the electrocardiogram data and the pulse data) which are detected respectively by the sensors, the receiver 30 which is the receiving side of the vital signs information can treat the sets of vital signs information (the electrocardiogram data and the pulse data) as if they are detected respectively by the first and second vital signs information detecting sensors 20A, 20B at the same time.

This is because, based on the first acceleration data and second acceleration data which are received in steps S38, S40, the receiver 30 causes the electrocardiogram data and the pulse data to be displayed on the display 31 in a synchronized state.

Second Embodiment

Next, a medical telemetry system 10A according to a second embodiment of the present disclosure will be described with reference to the accompanying drawings. In the drawings, components which correspond to each other are denoted by the same reference numerals or symbols. Duplicative description for such components will be omitted.

As illustrated in FIG. 1, a vital signs information synchronization system (hereinafter, referred to as the medical telemetry system 10A) includes a first vital signs information detecting sensor 20C, a second vital signs information detecting sensor 20D, an information processing device (hereinafter, referred to as the receiver 30), etc. In the case where the first vital signs information detecting sensor 20C and the second vital signs information detecting sensor 20D are not particularly distinguished from each other, the sensors will be hereinafter referred to as the vital signs information detecting sensor 20.

Figure 8A:
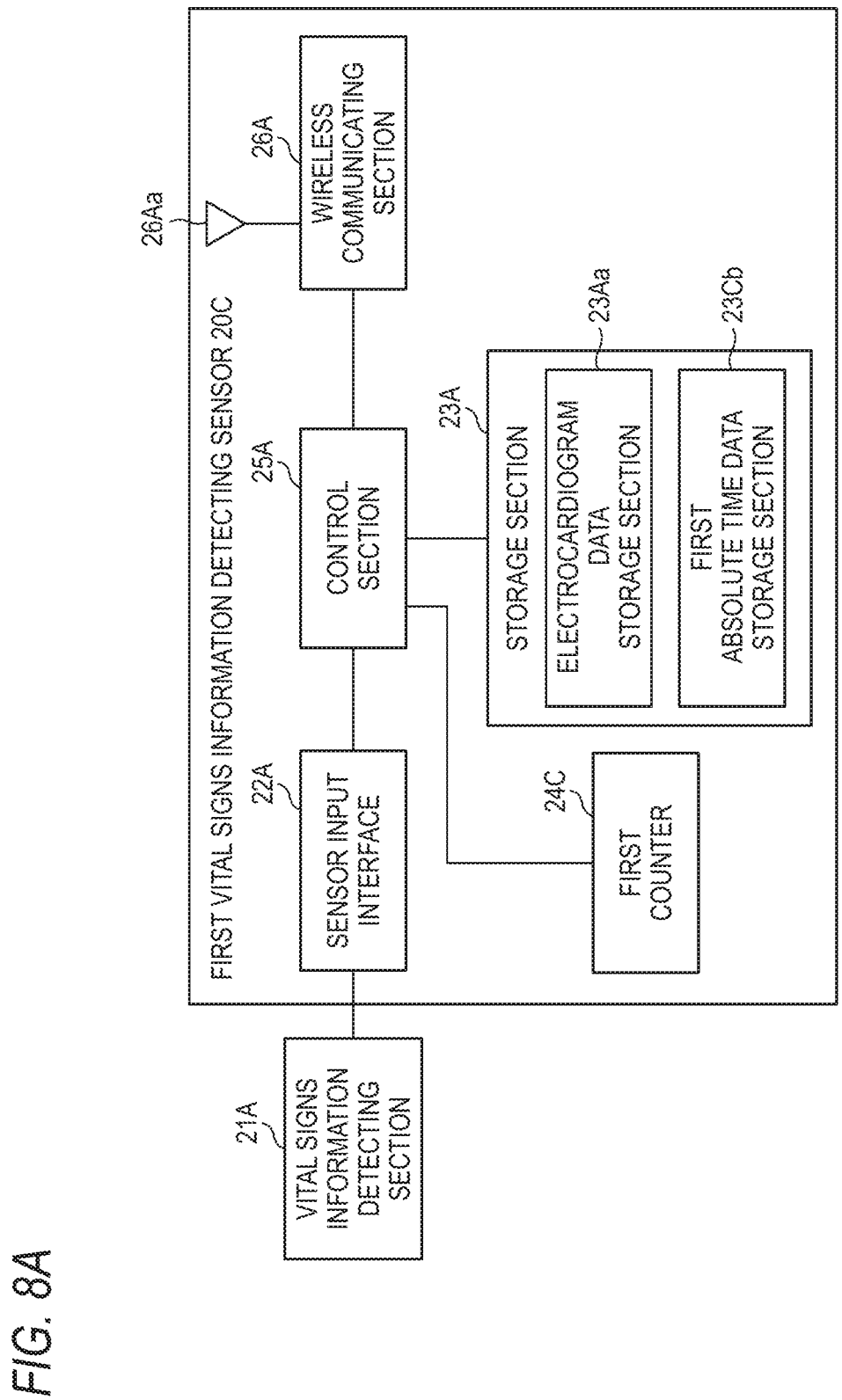
FIG. 8A is a schematic hardware diagram of a first vital signs information detecting sensor in a medical telemetry system of the second embodiment.

FIG. 8A is a schematic hardware diagram of the first vital signs information detecting sensor 20C.

As illustrated in FIG. 8A, the first vital signs information detecting sensor 20C in the embodiment corresponds to a sensor in which the first acceleration sensor 24A of the first vital signs information detecting sensor 20A in the first embodiment is replaced with a first counter 24C, and the first acceleration data storage section 23Ab of the first vital signs information detecting sensor 20A in the first embodiment is replaced with a first absolute time information storage section 23Cb.

Figure 8B:
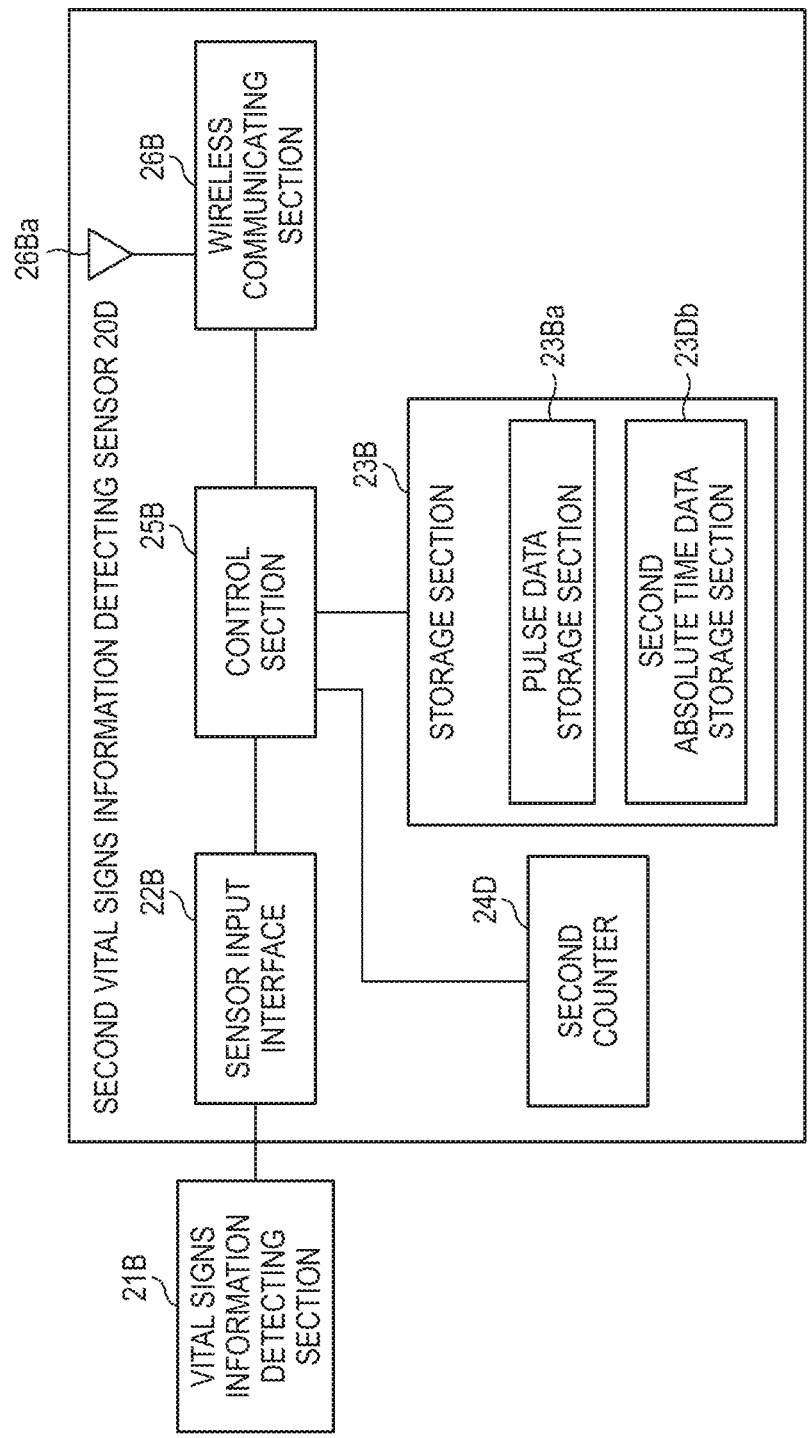
FIG. 8B is a schematic hardware diagram of a second vital signs information detecting sensor in the medical telemetry system of the second embodiment.

FIG. 8B is a schematic hardware diagram of the second vital signs information detecting sensor 20D.

The second vital signs information detecting sensor 20D in this embodiment corresponds to a sensor in which the second acceleration sensor 24B of the second vital signs information detecting sensor 20B in the first embodiment is replaced with a second counter 24D, and the second acceleration data storage section 23Bb of the second vital signs information detecting sensor 20B in the first embodiment is replaced with a second absolute time information storage section 23Db. The other configurations are identical with those of the first embodiment.

Hereinafter, description will be made by mainly focusing on the differences from the first embodiment.

The first counter 24C (the same is applied to the second counter 24D) counts the number of pulses of a pulse signal which is input to the first counter. In the case where the frequency of the input pulse signal is 500 Hz, for example, the first counter 24C (the same is applied to the second counter 24D) counts up every 2 msec.

The first absolute time information storage section 23Cb stores absolute time information (hereinafter, referred to as the first absolute time information) which is transmitted by the receiver 30, and received by the first vital signs information detecting sensor 20C. The second absolute time information storage section 23Db stores absolute time information (hereinafter, referred to as the second absolute time information) which is transmitted by the receiver 30, and received by the second vital signs information detecting sensor 20D.

[Operation Example of Medical Telemetry System 10A]

Figure 9:
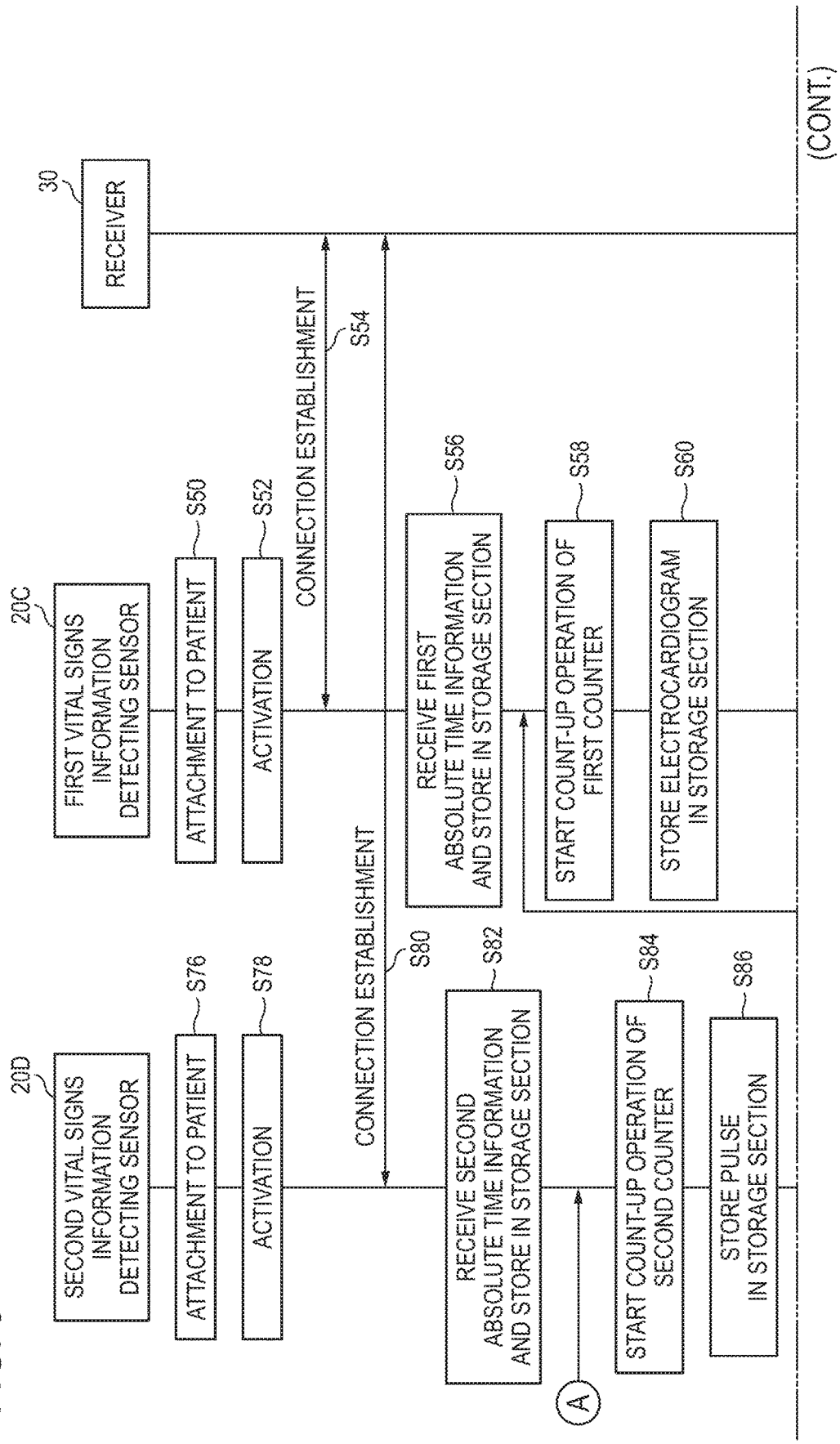
FIG. 9 is a sequence diagram illustrating the operation of the medical telemetry system of the second embodiment.
Figure 10:
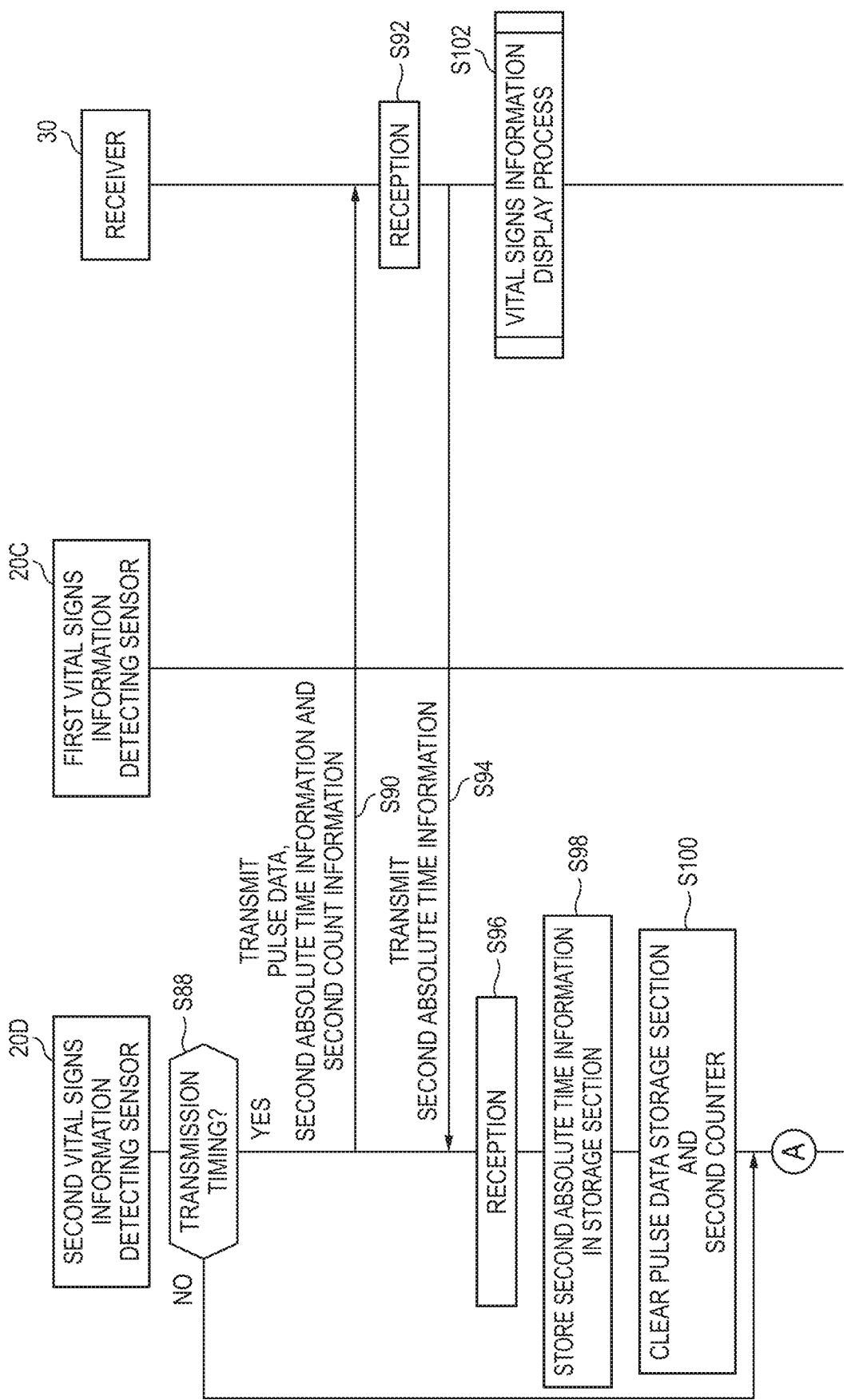
FIG. 10 is a sequence diagram illustrating the operation of the medical telemetry system of the second embodiment.

Next, an operation example of the medical telemetry system 10A will be described. FIGS. 9 and 10 are sequence diagrams illustrating the operation of the medical telemetry system 10A.

The following process of the receiver 30 is mainly implemented by the CPU of the receiver 30 with the execution of the predetermined application program 33a read from the storage section 33 into the RAM. Moreover, the following process of the vital signs information detecting sensor 20 is mainly implemented by the CPU of the vital signs information detecting sensor 20 with the execution of the control program read from the storage section 23A or 23B into the RAM.

First, the first vital signs information detecting sensor 20C is attached to the patient 50 as illustrated in FIG. 1 (step S50).

Next, when the first vital signs information detecting sensor 20C is activated with an unillustrated power switch (step S52), the first vital signs information detecting sensor 20C communicates with the receiver 30 according to the standard, thereby establishing a connection (step S54). During the process of establishing the connection, the receiver 30 acquires the first absolute time information from the clock section 36, and then transmits the acquired first absolute time information to the first vital signs information detecting sensor 20C.

When the first absolute time information transmitted by the receiver 30 is received, the first vital signs information detecting sensor 20C causes the received first absolute time information to be stored in the first absolute time information storage section 23Cb (step S56). The first vital signs information detecting sensor 20C then starts the count-up operation in the first counter 24C (step S58), and causes the electrocardiogram data of the patient 50 which are detected by the vital signs information detecting section 21A, to be stored in the electrocardiogram data storage section 23Aa (step S60).

When a transmission timing comes (step S62: Yes), the CPU of the first vital signs information detecting sensor 20C reads out the electrocardiogram data and the first absolute time information from the storage section 23A, reads out first count information (the counted value which is counted up by the first counter 24C) from the first counter 24C, and transmits the electrocardiogram data, first absolute time information, and first count information which are read out, to the receiver 30 through the wireless communicating section 26A (step S64). Alternatively, in place of the first absolute time information and the first count information, the CPU of the first vital signs information detecting sensor 20C may calculate a first time based on the first absolute time information and the first count information, and transmit the calculated first time to the receiver 30 through the wireless communicating section 26A. When the wireless communicating section 26A is set to a sleep state until the transmission timing comes, it is possible to save power consumption.

For example, the transmission timing is a timing when the electrocardiogram data stored in the storage section 23A exceed a threshold. When the count-up operation period in the first counter 24C is prolonged, there is a possibility that errors of the counted value in the first counter 24C (for example, errors of plus or minus 1 count) are accumulated, and the difference between the electrocardiogram data and pulse data which are displayed on the display 31 exceeds an allowable range. Therefore, it is preferable that the transmission timing (threshold) is so determined as to cause the difference between the electrocardiogram data and pulse data which are displayed on the display 31 to fall within the allowable range.

Alternatively, steps S60 and S62 may be omitted, and the electrocardiogram data of the patient 50 which are detected by the vital signs information detecting section 21A, and the like may be transmitted directly (without being stored in the storage section 23A) to the receiver 30.

When the first absolute time information transmitted by the receiver 30 is received (step S70), then, the CPU of the first vital signs information detecting sensor 20C causes the received first absolute time information to be stored in the first absolute time information storage section 23Cb (step S72).

The first vital signs information detecting sensor 20C then clears the electrocardiogram data storage section 23Aa and the first counter 24C (step S74). Namely, the stored contents of the electrocardiogram data storage section 23Aa are deleted, and the first counter 24C is reset.

Thereafter, the first vital signs information detecting sensor 20C repeatedly executes the processes of steps S58 to S64 and S70 to S74.

As described above, each time when the first vital signs information detecting sensor 20C receives the first absolute time information transmitted by the receiver 30 (step S70), the sensor clears the first counter 24C (step S74), and starts the count-up operation in the first counter 24C (step S58). As compared with the case where the count-up operation is continued without clearing the first counter 24C, therefore, the error of the counted value can be corrected.

Similarly, the second vital signs information detecting sensor 20D is attached to the patient 50 as illustrated in FIG. 1 (step S76).

Next, when the second vital signs information detecting sensor 20D is activated with an unillustrated power switch (step S78), the second vital signs information detecting sensor 20D communicates with the receiver 30 according to the standard, thereby establishing a connection (step S80). During the process of establishing the connection, the receiver 30 acquires the second absolute time information from the clock section 36, and then transmits the acquired second absolute time information to the second vital signs information detecting sensor 20D.

When the second absolute time information transmitted by the receiver 30 is received, the second vital signs information detecting sensor 20D causes the received second absolute time information to be stored in the second absolute time information storage section 23Db (step S82). The second vital signs information detecting sensor 20D then starts the count-up operation in the second counter 24D (step S84), and causes the pulse data of the patient 50 which are detected by the vital signs information detecting section 21B, to be stored in the pulse data storage section 23Ba (step S86).

When a transmission timing comes (step S88: Yes), then, the CPU of the second vital signs information detecting sensor 20D reads out the pulse data and the second absolute time information from the storage section 23B, and second count information (the counted value which is counted up by the second counter 24D) from the second counter 24D, and transmits the pulse data, second absolute time information, and second count information which are read out, to the receiver 30 through the wireless communicating section 26B (step S90). Alternatively, in place of the second absolute time information and the second count information, the CPU of the second vital signs information detecting sensor 20D may calculate a second time based on the second absolute time information and the second count information, and transmit the calculated second time to the receiver 30 through the wireless communicating section 26B. When the wireless communicating section 26B is set to a sleep state until the transmission timing comes, it is possible to save power consumption.

For example, the transmission timing is a timing when the pulse data stored in the storage section 23B exceed a threshold. When the count-up operation period in the second counter 24D is prolonged, there is a possibility that errors of the counted value in the second counter 24D (for example, errors of plus or minus 1 count) are accumulated, and the display mismatch between the electrocardiogram data and pulse data which are displayed on the display 31 exceeds an allowable range. Therefore, it is preferable that the transmission timing (threshold) is so determined as to cause the difference between the electrocardiogram data and pulse data which are displayed on the display 31 to fall within the allowable range.

Alternatively, steps S86 and S88 may be omitted, and the pulse data of the patient 50 which are detected by the vital signs information detecting section 21B, and the like may be transmitted directly (without being stored in the storage section 23B) to the receiver 30.

When the second absolute time information transmitted by the receiver 30 is received (step S96), the CPU of the second vital signs information detecting sensor 20D causes the received second absolute time information to be stored in the second absolute time information storage section 23Db (step S98).

The second vital signs information detecting sensor 20D then clears the pulse data storage section 23Ba and the second counter 24D (step S100). Namely, the stored contents of the pulse data storage section 23Ba are deleted, and the second counter 24D is reset.

Thereafter, the second vital signs information detecting sensor 20D repeatedly executes the processes of steps S84 to S90 and S96 to S100.

As described above, each time when the second vital signs information detecting sensor 20D receives the second absolute time information transmitted by the receiver 30 (step S96), the sensor clears the second counter 24D (step S100), and starts the count-up operation in the second counter 24D (step S84). As compared with the case where the count-up operation is continued without clearing the second counter 24D, therefore, the error of the counted value can be corrected.

When the electrocardiogram data, first absolute time information, and first count information which are transmitted by the first vital signs information detecting sensor 20C are received (step S66), the receiver 30 transmits the first absolute time information acquired from the clock section 36, for example, together with the ACK to the first vital signs information detecting sensor 20C (step S68). When the first absolute time information transmitted by the receiver 30 is received (step S70), the CPU of the first vital signs information detecting sensor 20C causes the received first absolute time information to be stored in the first absolute time information storage section 23Cb (step S72).

When the pulse data, second absolute time information, and second count information which are transmitted by the second vital signs information detecting sensor 20D are received (step S92), the receiver 30 transmits the second absolute time information acquired from the clock section 36, for example, together with the ACK to the second vital signs information detecting sensor 20D (step S94). When the second absolute time information transmitted by the receiver 30 is received (step S96), the CPU of the second vital signs information detecting sensor 20D causes the received second absolute time information to be stored in the second absolute time information storage section 23Db (step S98).

Figure 11:
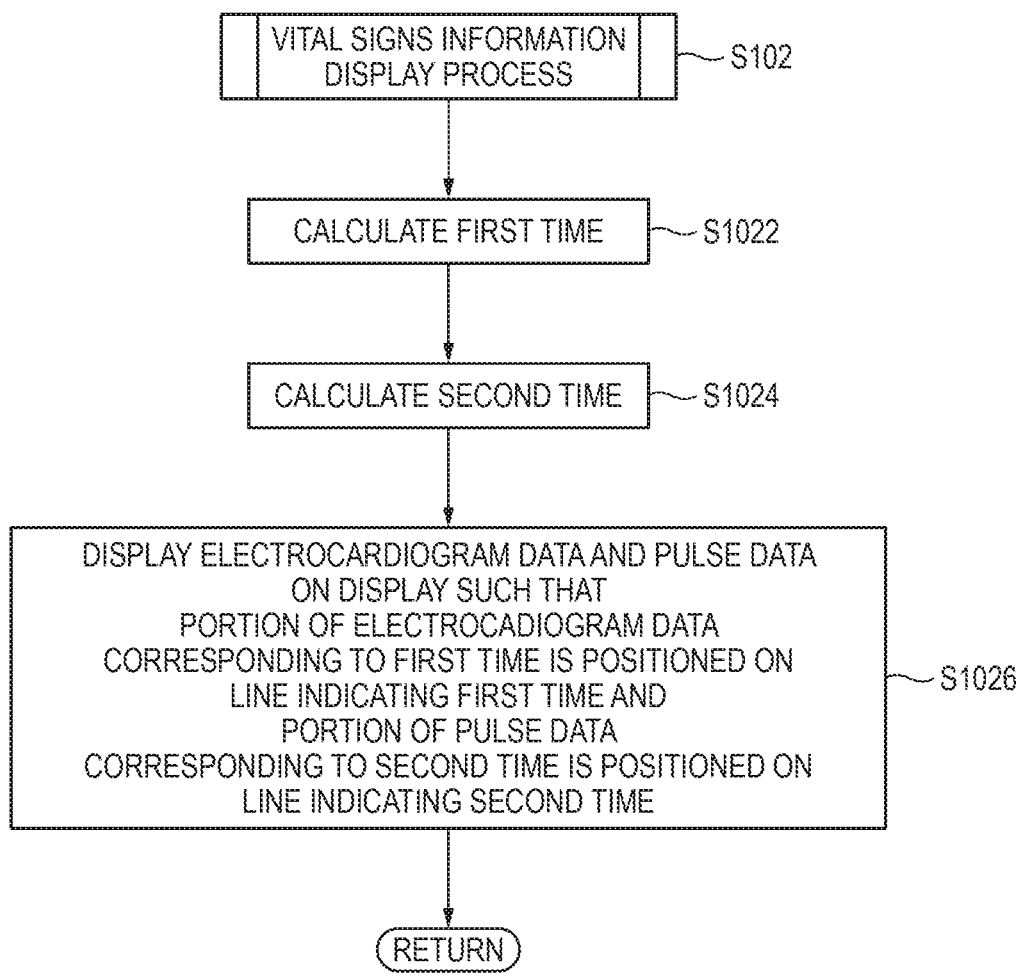
FIG. 11 is a flowchart illustrating a vital signs information display process of the second embodiment.

Next, the receiver 30 executes the vital signs information display process (step S102). FIG. 11 is a flowchart illustrating the vital signs information display process. The vital signs information display process is a process in which the receiver 30 causes the electrocardiogram data and the pulse data to be displayed on the display 31 in a synchronized state.

Specifically, the CPU of the receiver 30 first calculates the first time based on the first absolute time information and first count information which are received in the step S66 (step S1022). In the case where the first absolute time information indicates 10:01:00, and the first counter 24C counts up every 2 msec, for example, the first time can be calculated by multiplying 2 msec with the counted value of the first counter 24C and adding the obtained value to 10:01:00. In the case where the first time which is calculated based on the first absolute time information and the first count information is received in step S66, the step S1022 is omitted.

Next, the CPU of the receiver 30 calculates the second time based on the second absolute time information and second count information which are received in the step S92 (step S1024). In the case where the second absolute time information indicates 10:11:00, and the second counter 24D counts up every 2 msec, for example, the second time can be calculated by multiplying 2 msec with the counted value of the second counter 24D and adding the obtained value to 10:11:00. In the case where the second time which is calculated based on the second absolute time information and the second count information is received in the step S92, the step S1024 is omitted.

Figure 12:
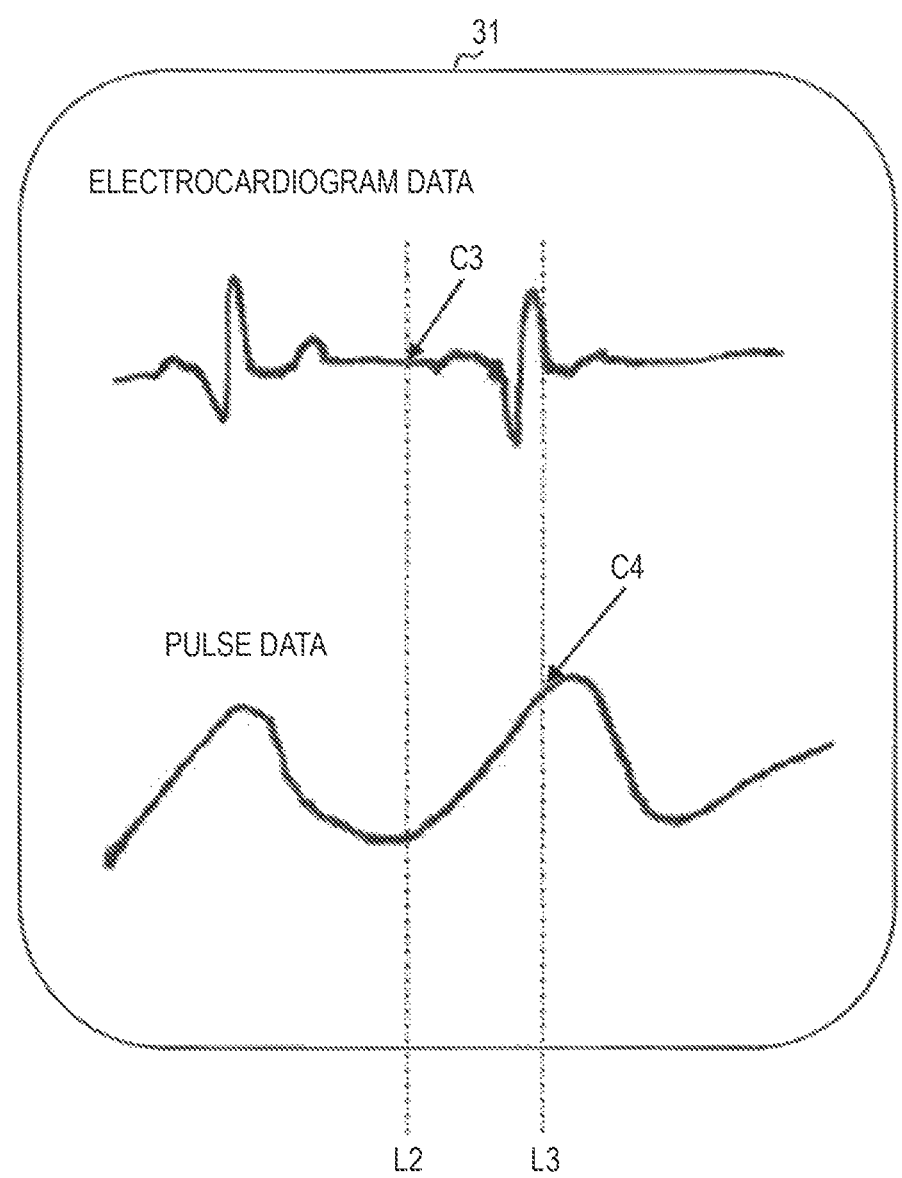
FIG. 12 illustrates display examples of the electrocardiogram data and the pulse data according to the second embodiment.

Next, the CPU of the receiver 30 causes the electrocardiogram data and the pulse data to be displayed on the display 31 so that a portion C3 (see FIG. 12) of the electrocardiogram data corresponding to the first time is positioned on a line L2 indicating the first time, and a portion C4 (see FIG. 12) of the pulse data corresponding to the second time is positioned on a line L3 indicating the second time (step S1026). Namely, the electrocardiogram data and the pulse data are displayed on the display 31 in a synchronized state. The lines L2, L3 may be displayed on the display 31, or may not be displayed.

In the electrocardiogram data, in the case where the sampling frequency is 500 Hz, and the first counter 24C counts up every 2 msec, for example, the portion C3 corresponding to the first time is configured by n-th data from the beginning of the sampled electrocardiogram data (data group). Here, "n" represents the counted value of the first counter 24C. In the pulse data, in the case where the sampling frequency is 500 Hz, and the second counter 24D counts up every 2 msec, for example, the portion C4 corresponding to the second time is configured by m-th data from the beginning of the sampled pulse data (data group). Here, "m" represents the counted value of the second counter 24D.

As described above, according to this embodiment, even when the first and second vital signs information detecting sensors 20C, 20D wirelessly transmit at different timings the sets of vital signs information (the electrocardiogram data and the pulse data) which are detected respectively by the sensors, the receiver 30 which is the receiving side of the vital signs information can treat the sets of vital signs information (the electrocardiogram data and the pulse data) as if they are detected respectively by the first and second vital signs information detecting sensors 20C, 20D at the same time.

This is because, based on the first absolute time information and first count information which are received in the step S66, and the second absolute time information and second count information which are received in the step S92 (based on the first time and the second time), the electrocardiogram data and the pulse data are displayed on the display 31 in a synchronized state.

Third Embodiment

Next, a medical telemetry system 10B according to a third embodiment of the present disclosure will be described with reference to the accompanying drawings. In the drawings, components which correspond to each other are denoted by the same reference numerals or symbols. Duplicative description for such components will be omitted.

As illustrated in FIG. 1, a vital signs information synchronization system (hereinafter, referred to as the medical telemetry system 10B) includes a first vital signs information detecting sensor 20E, a second vital signs information detecting sensor 20F, an information processing device (hereinafter, referred to as the receiver 30), etc. In the case where the first vital signs information detecting sensor 20E and the second vital signs information detecting sensor 20F are not particularly distinguished from each other, the sensors will be hereinafter referred to as the vital signs information detecting sensor 20.

Figure 13A:
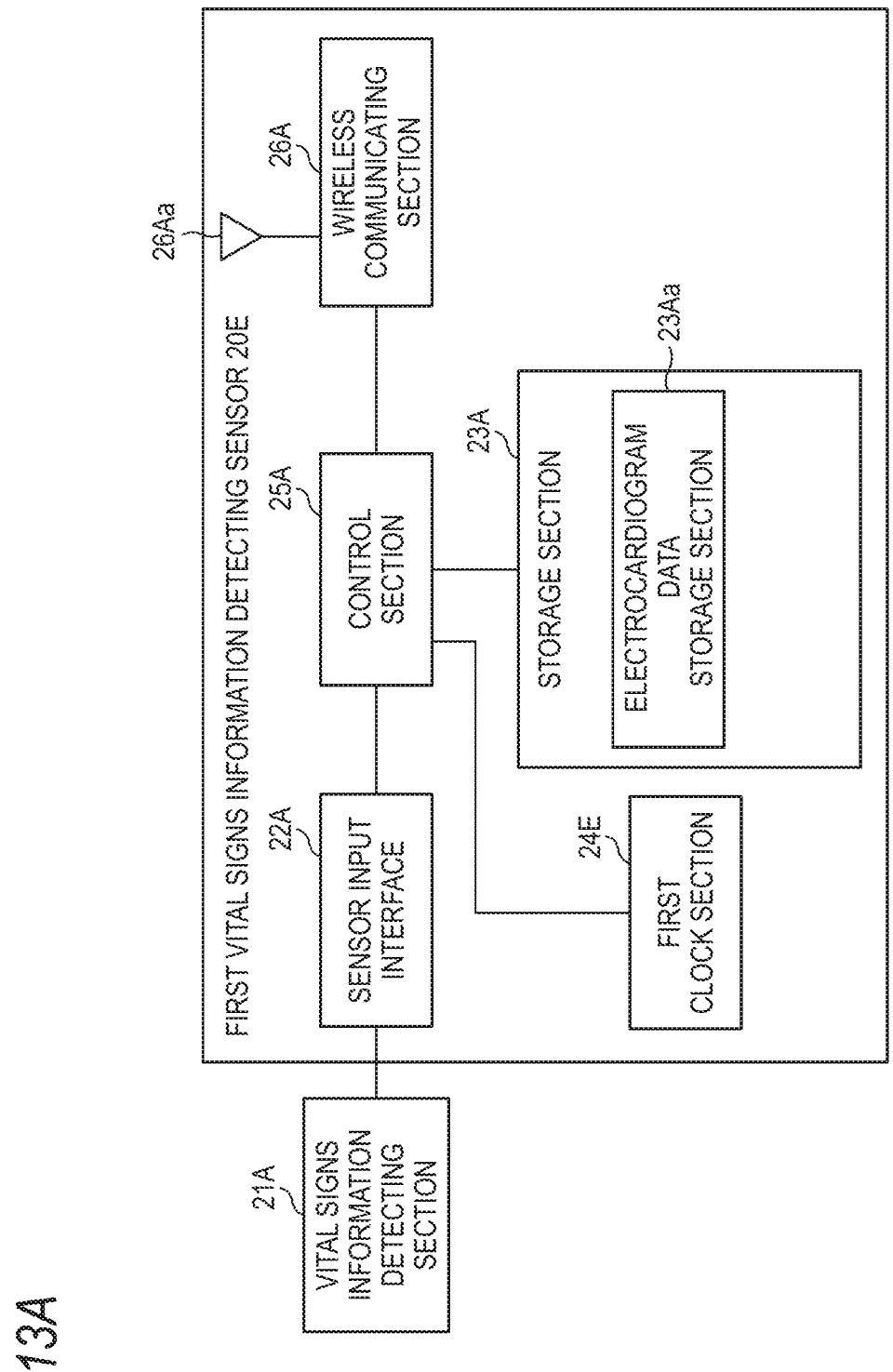
FIG. 13A is a schematic hardware diagram of a first vital signs information detecting sensor in a medical telemetry system of the third embodiment.

FIG. 13A is a schematic hardware diagram of the first vital signs information detecting sensor 20E.

As illustrated in FIG. 13A, the first vital signs information detecting sensor 20E in this embodiment corresponds to a sensor in which the first counter 24C of the first vital signs information detecting sensor 20C in the second embodiment is replaced with a first clock section 24E.

Figure 13B:
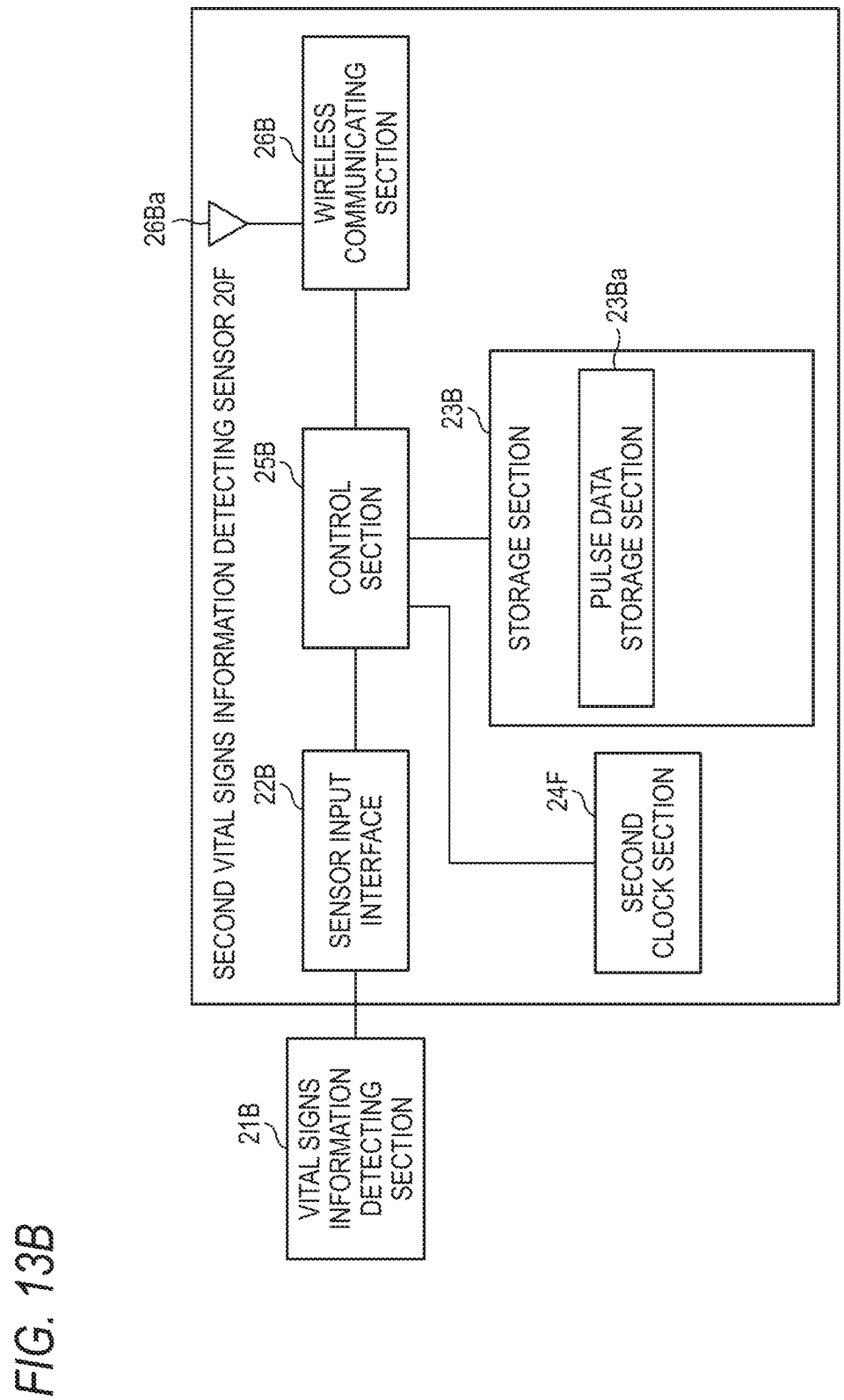
FIG. 13B is a schematic hardware diagram of a second vital signs information detecting sensor in the medical telemetry system of the third embodiment.

FIG. 13B is a schematic hardware diagram of the second vital signs information detecting sensor 20F.

The second vital signs information detecting sensor 20F in this embodiment corresponds to a sensor in which the second counter 24D of the second vital signs information detecting sensor 20D in the second embodiment is replaced with a second clock section 24F. The other configurations are identical with those of the second embodiment.

Hereinafter, description will be made by mainly focusing on differences from the second embodiment.

The first clock section 24E is a clock which is incorporated in the first vital signs information detecting sensor 20E, such as a real-time clock. The first clock section 24E starts the time count operation from the first absolute time information (specifically, the time indicated by the first absolute time information) which is received by the wireless communicating section 26A. In the case where the wireless communicating section 26A receives the first absolute time information which is transmitted by the receiver 30, specifically, the first vital signs information detecting sensor 20E (the control section 25A) sets the received first absolute time information to the first clock section 24E. The first clock section 24E starts the time count operation from the set first absolute time information. When an unillustrated power switch of the first vital signs information detecting sensor 20E is on, the first clock section 24E is powered by a built-in power supply (for example, a button battery) to perform the time count operation. When the power switch of the first vital signs information detecting sensor 20E is off, the first clock section 24E is not powered from the view point of electric power saving, so that the time count operation is not performed.

The second clock section 24F is a clock which is incorporated in the second vital signs information detecting sensor 20F, such as a real-time clock. The second clock section 24F starts the time count operation from the second absolute time information (specifically, the time indicated by the second absolute time information) which is received by the wireless communicating section 26B. In the case where the wireless communicating section 26B receives the second absolute time information which is transmitted by the receiver 30, specifically, the second vital signs information detecting sensor 20F (the control section 25B) sets the received second absolute time information to the second clock section 24F. The second clock section 24F starts the time count operation from the set second absolute time information. When an unillustrated power switch of the second vital signs information detecting sensor 20F is on, the second clock section 24F is powered by a built-in power supply (for example, a button battery) to perform the time count operation. When the power switch of the second vital signs information detecting sensor 20F is off, the second clock section 24F is not powered from the view point of electric power saving, so that the time count operation is not performed.

[Operation Example of Medical Telemetry System 10B]

Figure 14:
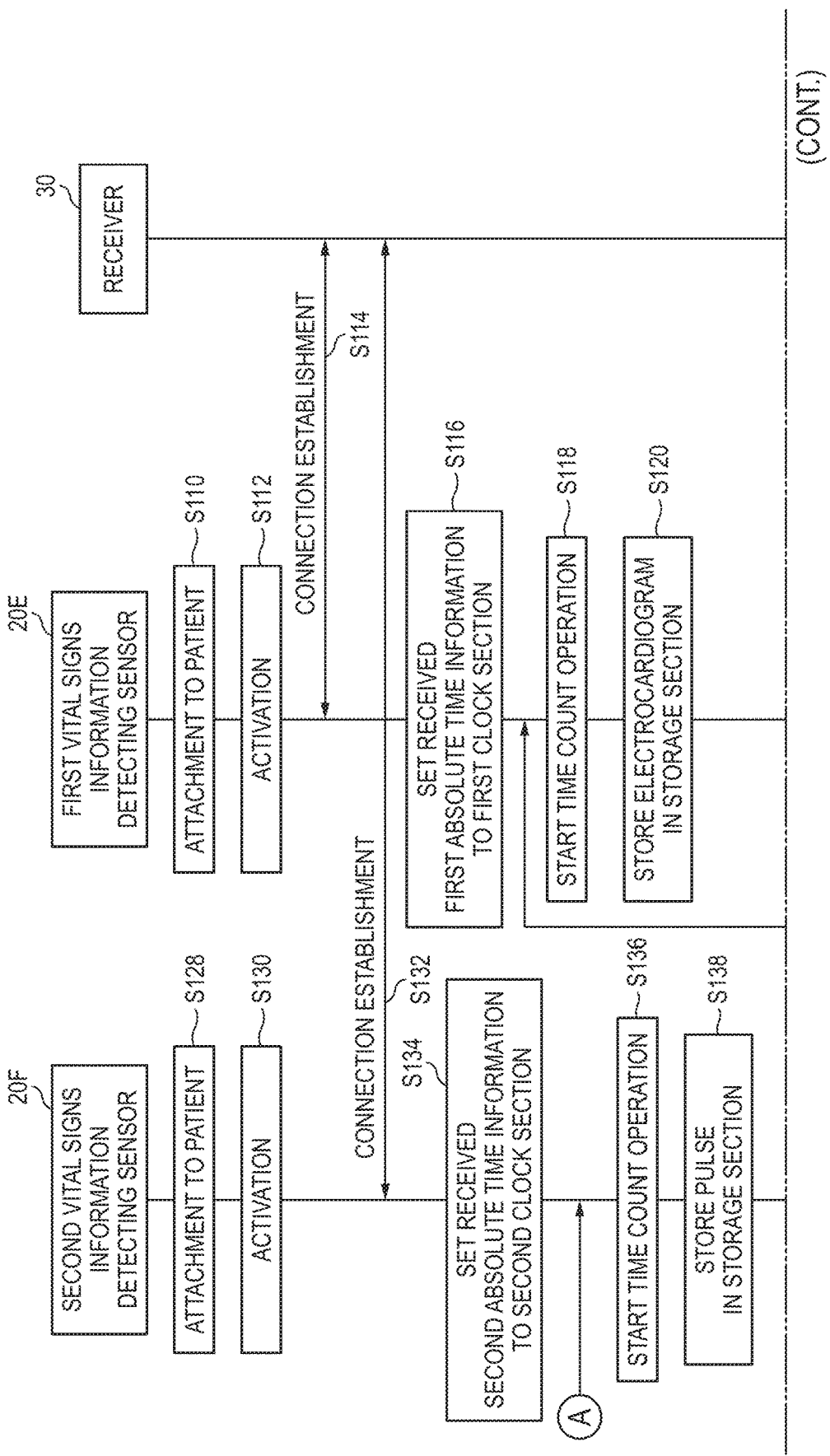
FIG. 14 is a sequence diagram illustrating the operation of the medical telemetry system of the third embodiment.
Figure 15:
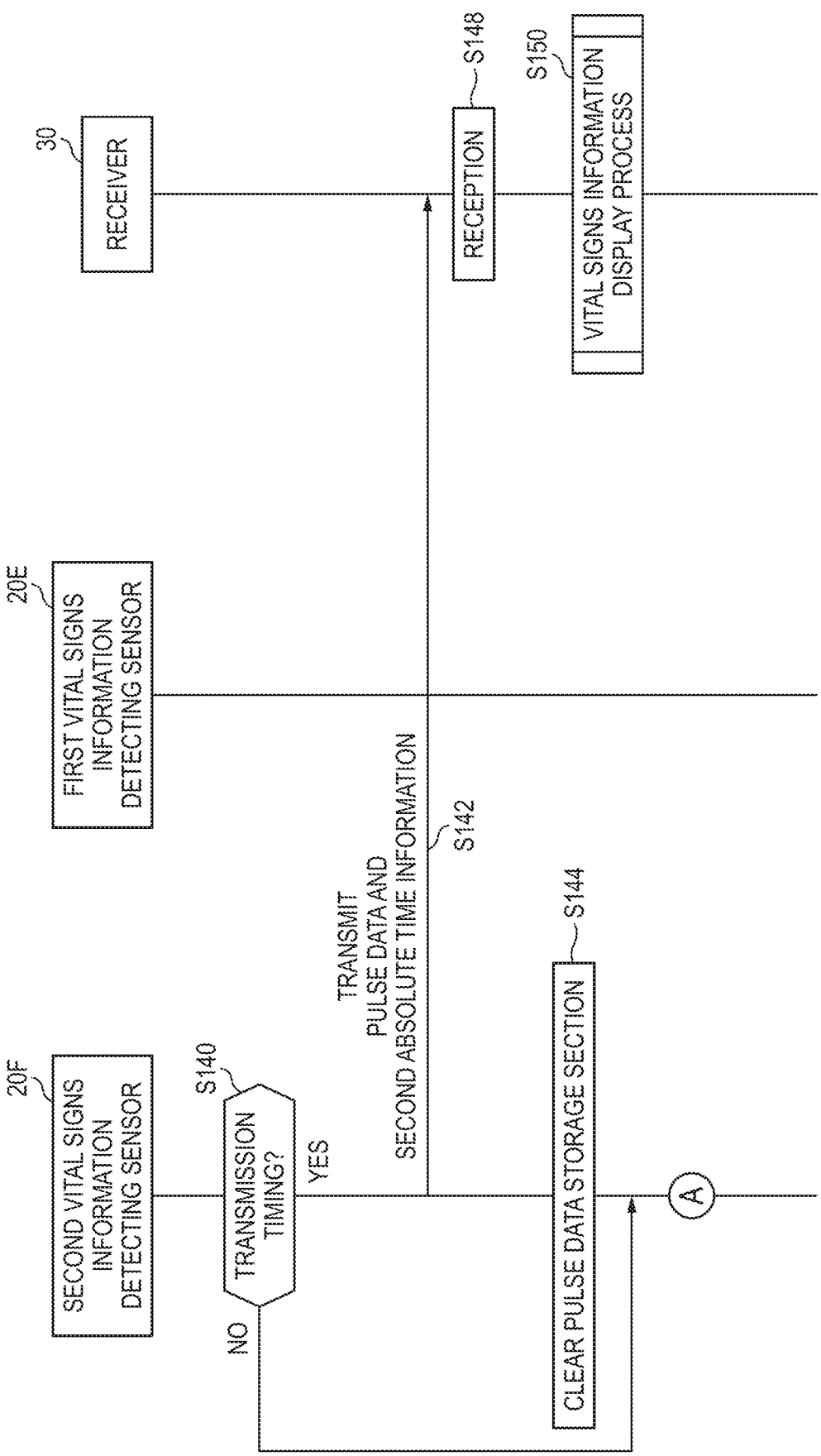
FIG. 15 is a sequence diagram illustrating the operation of the medical telemetry system of the third embodiment.

Next, an operation example of the medical telemetry system 10B will be described. FIGS. 14 and 15 are sequence diagrams illustrating the operation of the medical telemetry system 10B.

The following process of the receiver 30 is mainly implemented by the CPU of the receiver 30 with the execution of the predetermined application program 33a read from the storage section 33 into the RAM. Moreover, the following process of the vital signs information detecting sensor 20 is mainly implemented by the CPU of the vital signs information detecting sensor 20 with the execution of the control program read from the storage section 23A or 23B into the RAM.

First, the first vital signs information detecting sensor 20E is attached to the patient 50 as illustrated in FIG. 1 (step S110).

Next, when the first vital signs information detecting sensor 20E is activated (step S112) with an unillustrated power switch, the first vital signs information detecting sensor 20E supplies power to the first clock section 24E. The first vital signs information detecting sensor 20E then communicates with the receiver 30 according to the standard, thereby establishing a connection (step S114). During the process of establishing the connection, the receiver 30 acquires the first absolute time information from the clock section 36, and then transmits the acquired first absolute time information to the first vital signs information detecting sensor 20E.

When the wireless communicating section 26A receives the first absolute time information transmitted by the receiver 30, the first vital signs information detecting sensor 20E sets the received first absolute time information to the first clock section 24E (step S116). The first clock section 24E starts the time count operation from the set first absolute time information (step S118). The first vital signs information detecting sensor 20E then causes the electrocardiogram data of the patient 50 which are detected by the vital signs information detecting section 21A, to be stored in the electrocardiogram data storage section 23Aa (step S120).

When a transmission timing comes (step S122: Yes), the CPU of the first vital signs information detecting sensor 20E reads out the electrocardiogram data from the storage section 23A, acquires first time information from the first clock section 24E, and transmits the electrocardiogram data which are read out, and the acquired first time information, to the receiver 30 through the wireless communicating section 26A (step S124). When the wireless communicating section 26A is set to a sleep state until the transmission timing comes, it is possible to save power consumption.

For example, the transmission timing is a timing when the electrocardiogram data stored in the storage section 23A exceed a threshold. For example, the first time information is information indicating a timing when the electrocardiogram data stored in the storage section 23A exceed the threshold.

Alternatively, steps S120 and S122 may be omitted, and the electrocardiogram data of the patient 50 which are detected by the vital signs information detecting section 21A, and the like may be transmitted directly (without being stored in the storage section 23A) to the receiver 30.

The first vital signs information detecting sensor 20E then clears the electrocardiogram data storage section 23Aa (step S126). Namely, the stored contents of the electrocardiogram data storage section 23Aa are deleted.

Thereafter, the first vital signs information detecting sensor 20E repeatedly executes the processes of steps S118 to S126.

Similarly, the second vital signs information detecting sensor 20F is attached to the patient 50 as illustrated in FIG. 1 (step S128).

Next, when the second vital signs information detecting sensor 20F is activated with an unillustrated power switch (step S130), the second vital signs information detecting sensor 20F supplies power to the second clock section 24F. The second vital signs information detecting sensor 20F then communicates with the receiver 30 according to the standard, thereby establishing a connection (step S132). During the process of establishing the connection, the receiver 30 acquires the second absolute time information from the clock section 36, and then transmits the acquired second absolute time information to the second vital signs information detecting sensor 20F.

When the wireless communicating section 26B receives the second absolute time information transmitted by the receiver 30, the second vital signs information detecting sensor 20F sets the received second absolute time information to the second clock section 24F (step S134). The second clock section 24F starts the time count operation from the set second absolute time information (step S136). The second vital signs information detecting sensor 20F then causes the pulse data of the patient 50 which are detected by the vital signs information detecting section 21B, to be stored in the pulse data storage section 23Ba (step S138).

When a transmission timing comes (step S140: Yes), the CPU of the second vital signs information detecting sensor 20F reads out the pulse data from the storage section 23B, acquires second time information from the second clock section 24F, and transmits the pulse data which are read out, and the acquired second time information, to the receiver 30 through the wireless communicating section 26B (step S142). When the wireless communicating section 26B is set to a sleep state until the transmission timing comes, it is possible to save power consumption.

For example, the transmission timing is a timing when the pulse data stored in the storage section 23B exceed a threshold. For example, the second time information is information indicating a timing when the pulse data stored in the storage section 23B exceed the threshold.

Alternatively, steps S138 and S140 may be omitted, and the pulse data of the patient 50 which are detected by the vital signs information detecting section 21B, and the like may be transmitted directly (without being stored in the storage section 23B) to the receiver 30.

The second vital signs information detecting sensor 20F then clears the pulse data storage section 23Ba (step S144). Namely, the stored contents of the pulse data storage section 23Ba are deleted.

Thereafter, the second vital signs information detecting sensor 20F repeatedly executes the processes of the steps S136 to S144.

When the electrocardiogram data and first time information which are transmitted by the first vital signs information detecting sensor 20E are received (step S146), and the pulse data and second time information which are transmitted by the second vital signs information detecting sensor 20F are received (step S148), the receiver 30 executes the vital signs information display process (step S150). The vital signs information display process is a process in which the receiver 30 causes the electrocardiogram data and the pulse data to be displayed on the display 31 in a synchronized state.

Figure 16:
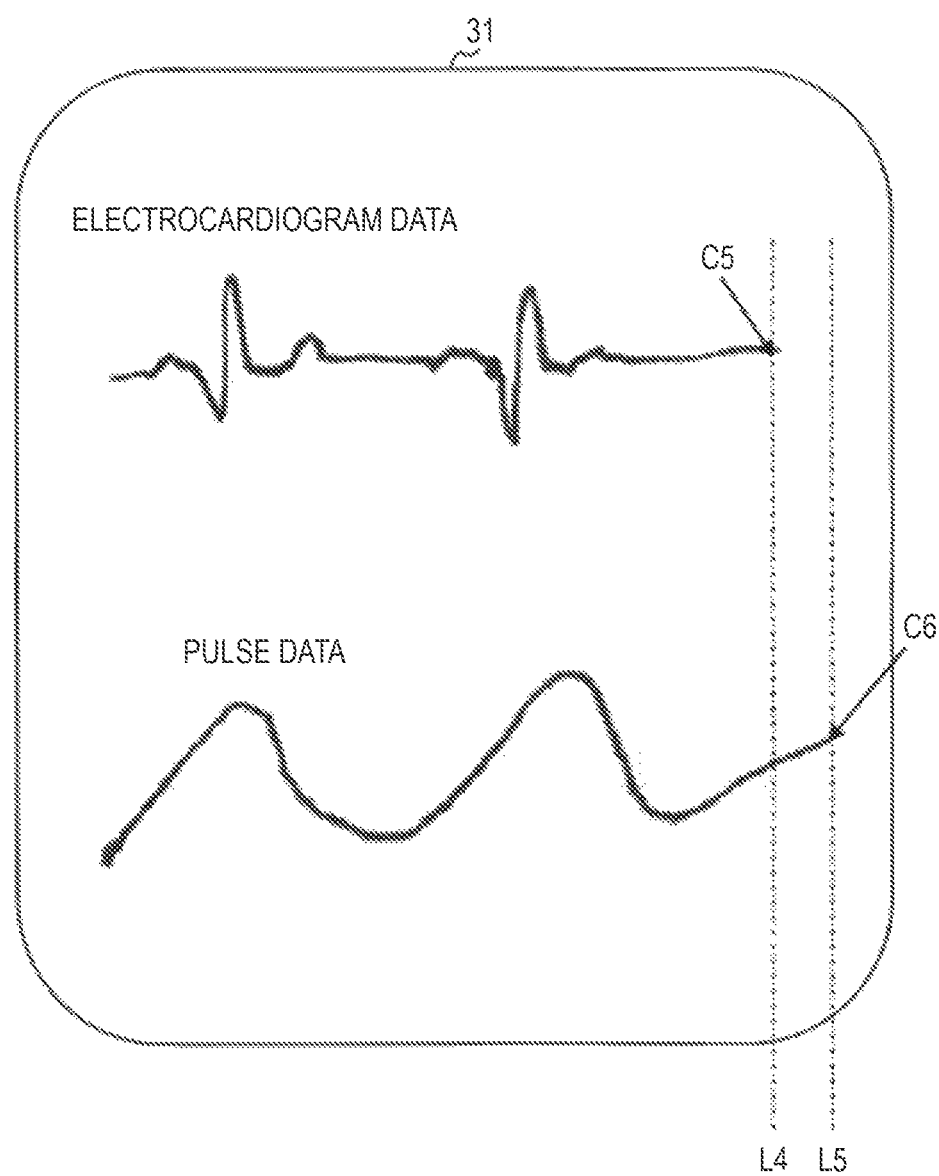
FIG. 16 illustrates display examples of the electrocardiogram data and the pulse data according to the third embodiment.

Specifically, the CPU of the receiver 30 causes the electrocardiogram data and the pulse data to be displayed on the display 31 so that a portion C5 (see FIG. 16) of the electrocardiogram data corresponding to the first time (the time indicated by the first absolute time information) is positioned on a line L4 indicating the first time, and a portion C6 (see FIG. 16) of the pulse data corresponding to the second time (the time indicated by the second absolute time information) is positioned on a line L5 indicating the second time. Namely, the electrocardiogram data and the pulse data are displayed on the display 31 in a synchronized state. The lines L4, L5 may be displayed on the display 31, or may not be displayed.

According to this embodiment, even when the first and second vital signs information detecting sensors 20E, 20F wirelessly transmit at different timings the sets of vital signs information (the electrocardiogram data and the pulse data) which are detected respectively by the sensors, as described above, the receiver 30 which is the receiving side of the vital signs information can treat the sets of vital signs information (the electrocardiogram data and the pulse data) as if they are detected respectively by the first and second vital signs information detecting sensors 20E, 20F at the same time.

This is because, based on the first time information which is received in the step S146, and the second time information which is received in the step S148, the electrocardiogram data and the pulse data are displayed on the display 31 in a synchronized state.

Fourth Embodiment

Next, a medical telemetry system 10C which is a fourth embodiment of the present disclosure will be described with reference to the accompanying drawings. In the drawings, components which correspond to each other are denoted by the same reference numerals or symbols. Duplicative description for such components will be omitted.

As illustrated in FIG. 1, a vital signs information synchronization system (hereinafter, referred to as the medical telemetry system 10C) includes a first vital signs information detecting sensor 20G a second vital signs information detecting sensor 20H, an information processing device (hereinafter, referred to as the receiver 30), etc. In the case where the first vital signs information detecting sensor 20G and the second vital signs information detecting sensor 20H are not particularly distinguished from each other, the sensors will be hereinafter referred to as the vital signs information detecting sensor 20.

Figure 17A:
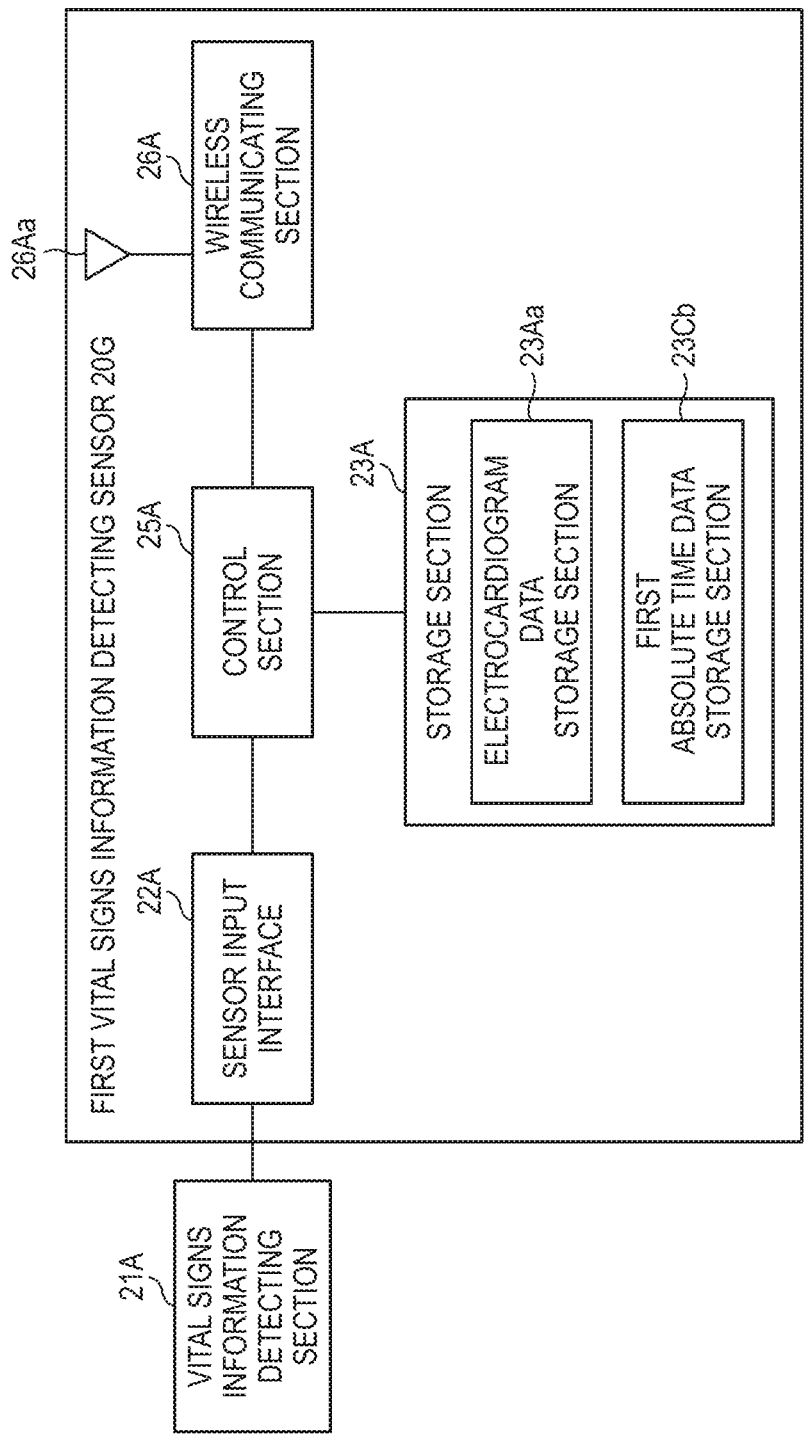
FIG. 17A is a schematic hardware diagram of a first vital signs information detecting sensor in a medical telemetry system of the fourth embodiment.

FIG. 17A is a schematic hardware diagram of the first vital signs information detecting sensor 20G.

The first vital signs information detecting sensor 20G in this embodiment corresponds to a sensor in which the first counter 24C of the first vital signs information detecting sensor 20C in the second embodiment is omitted. The other configurations are identical with those of the second embodiment.

Figure 17B:
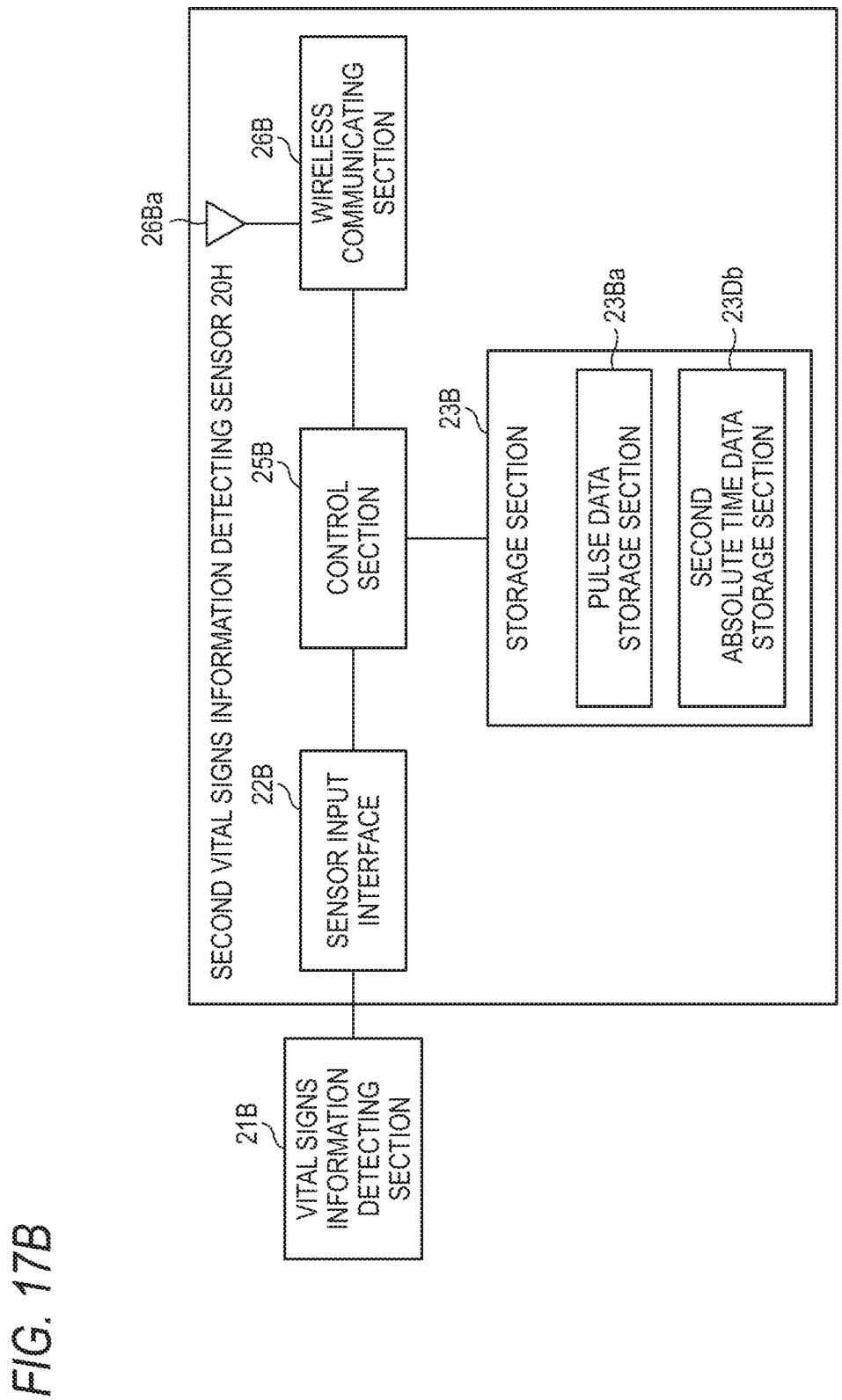
FIG. 17B is a schematic hardware diagram of a second vital signs information detecting sensor in the medical telemetry system of the fourth embodiment.

FIG. 17B is a schematic hardware diagram of the second vital signs information detecting sensor 20H.

The second vital signs information detecting sensor 20H in this embodiment corresponds to a sensor in which the second counter 24D of the second vital signs information detecting sensor 20D in the second embodiment is omitted. The other configurations are identical with those of the second embodiment.

Hereinafter, description will be made by mainly focusing on differences from the second embodiment.

[Operation Example of Medical Telemetry System 10C]

Figure 18:
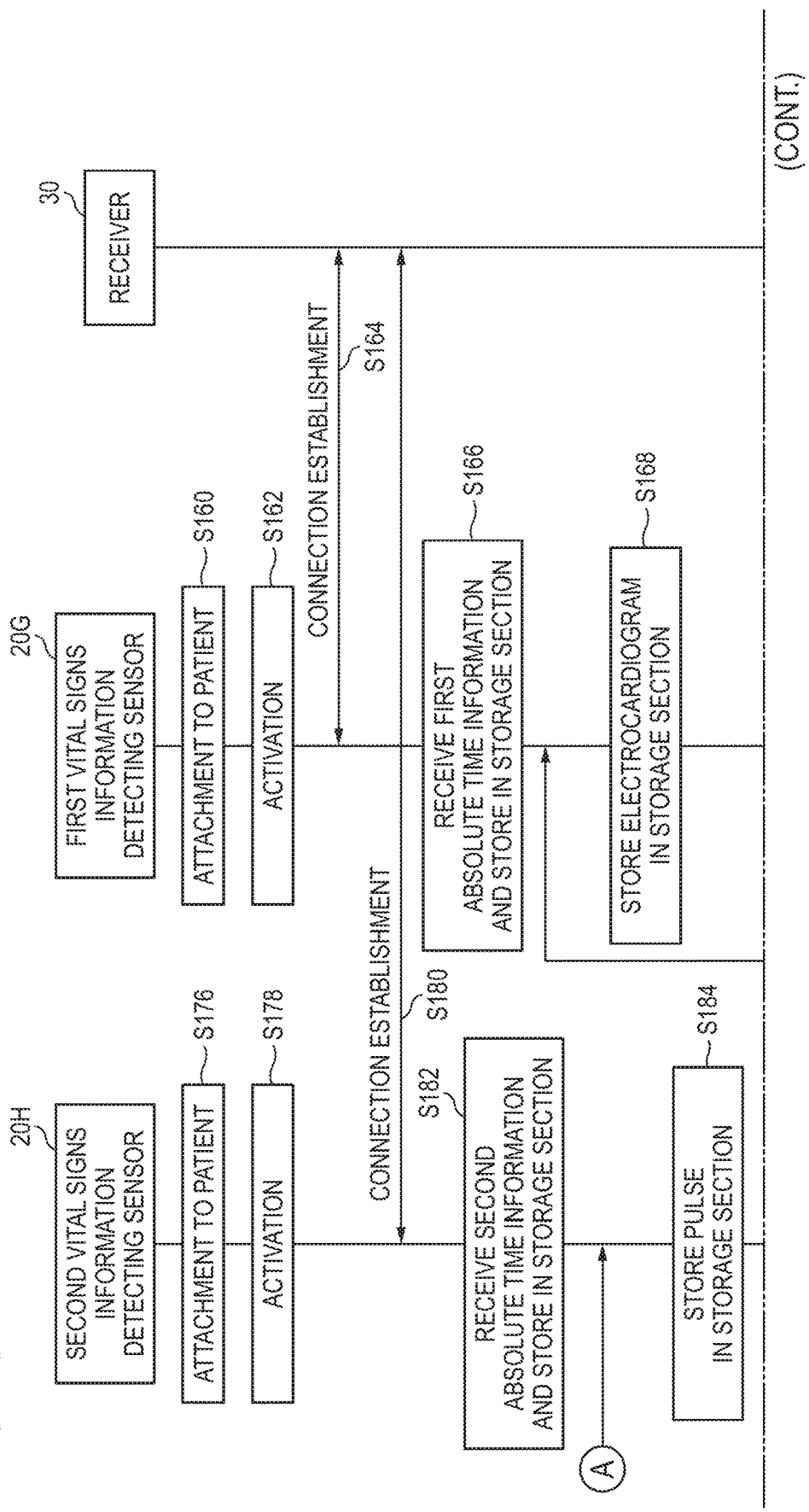
FIG. 18 is a sequence diagram illustrating the operation of the medical telemetry system of the fourth embodiment.
Figure 19:
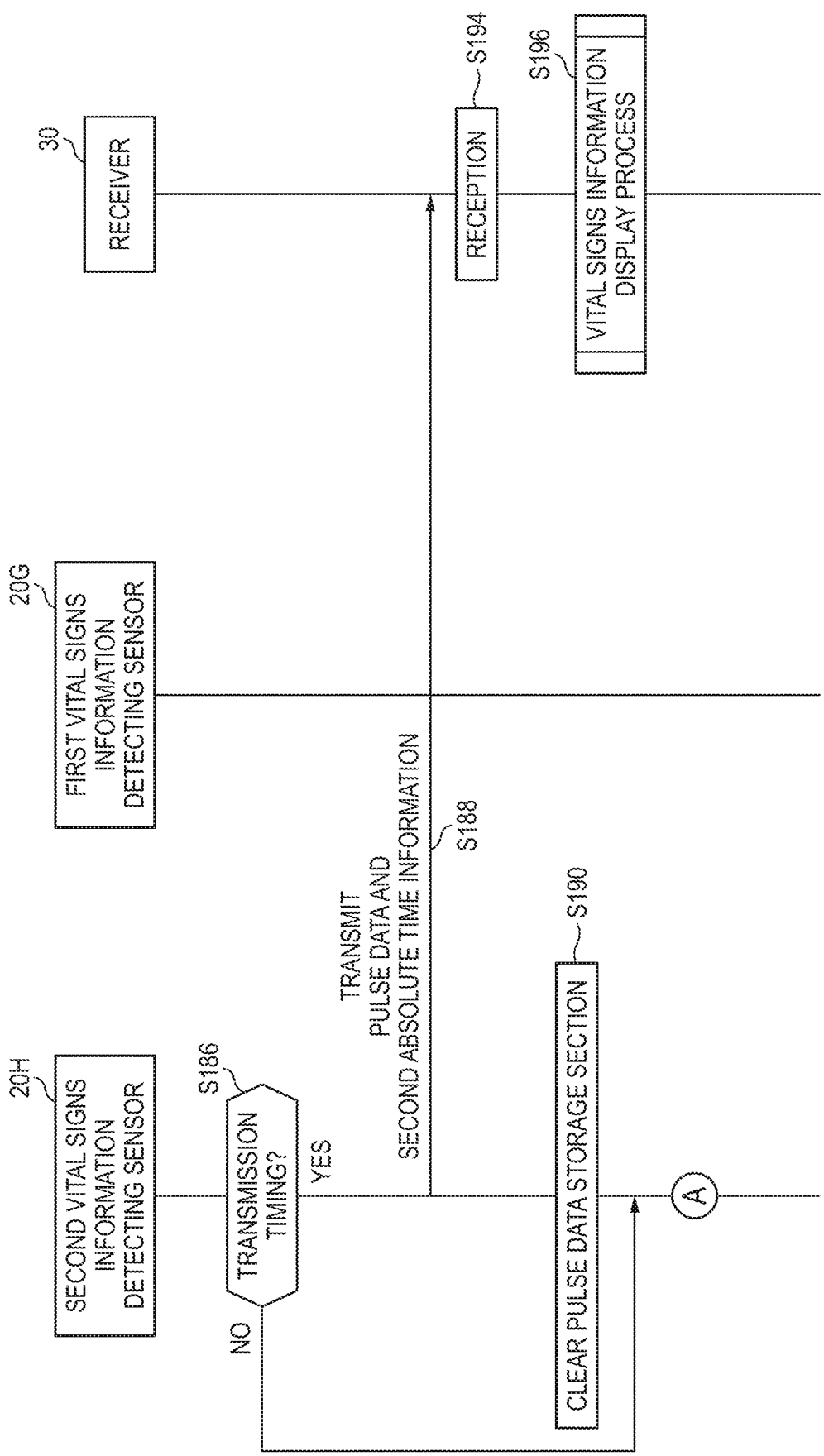
FIG. 19 is a sequence diagram illustrating the operation of the medical telemetry system of the fourth embodiment.

Next, an operation example of the medical telemetry system 10C will be described. FIGS. 18 and 19 are sequence diagrams illustrating the operation of the medical telemetry system 10C.

The following process of the receiver 30 is mainly implemented by the CPU of the receiver 30 with the execution of the predetermined application program 33a read from the storage section 33 into the RAM. Moreover, the following process of the vital signs information detecting sensor 20 is mainly implemented by the CPU of the vital signs information detecting sensor 20 with the execution of the control program read from the storage section 23A or 23B into the RAM.

First, the first vital signs information detecting sensor 20G is attached to the patient 50 as illustrated in FIG. 1 (step S160).

Next, when the first vital signs information detecting sensor 20G is activated with an unillustrated power switch (step S162), the first vital signs information detecting sensor 20G communicates with the receiver 30 according to the standard, thereby establishing a connection (step S164). During the process of establishing the connection, the receiver 30 acquires the first absolute time information from the clock section 36, and then transmits the acquired first absolute time information to the first vital signs information detecting sensor 20G.

When the wireless communicating section 26A receives the first absolute time information transmitted by the receiver 30, the first vital signs information detecting sensor 20G causes the received first absolute time information to be stored in the first absolute time information storage section 23Cb (step S166). The first vital signs information detecting sensor 20G then causes the electrocardiogram data of the patient 50 which are detected by the vital signs information detecting section 21A, to be stored in the electrocardiogram data storage section 23Aa (step S168). In this case, the first absolute time information indicates, for example, a timing when the storage of the electrocardiogram data is started (i.e., the time of the beginning of the electrocardiogram data).

When a transmission timing comes (step S170: Yes), the CPU of the first vital signs information detecting sensor 20G reads out the electrocardiogram data and the first absolute time information from the storage section 23A, and transmits the electrocardiogram data and first absolute time information which are read out, to the receiver 30 through the wireless communicating section 26A (step S172). When the wireless communicating section 26A is set to a sleep state until the transmission timing comes, it is possible to save power consumption.

For example, the transmission timing is a timing when the electrocardiogram data stored in the storage section 23A exceed a threshold.

Alternatively, steps S168 and S170 may be omitted, and the electrocardiogram data of the patient 50 which are detected by the vital signs information detecting section 21A, and the like may be transmitted directly (without being stored in the storage section 23A) to the receiver 30.

The first vital signs information detecting sensor 20G clears the electrocardiogram data storage section 23Aa (step S174). Namely, the stored contents of the electrocardiogram data storage section 23Aa are deleted.

Thereafter, the first vital signs information detecting sensor 20G repeatedly executes the processes of steps S168 to S174.

Similarly, the second vital signs information detecting sensor 20H is attached to the patient 50 as illustrated in FIG. 1 (step S176).

Next, when the second vital signs information detecting sensor 20H is activated with an unillustrated power switch (step S178), the second vital signs information detecting sensor 20H communicates with the receiver 30 according to the standard, thereby establishing a connection (step S180). During the process of establishing the connection, the receiver 30 acquires the second absolute time information from the clock section 36, and then transmits the acquired second absolute time information to the second vital signs information detecting sensor 20H.

When the wireless communicating section 26B receives the second absolute time information transmitted by the receiver 30, the second vital signs information detecting sensor 20H causes the received second absolute time information to be stored in the second absolute time information storage section 23Db (step S182). The second vital signs information detecting sensor 20H then causes the pulse data of the patient 50 which are detected by the vital signs information detecting section 21B, to be stored in the pulse data storage section 23Ba (step S184). In this case, the second absolute time information indicates, for example, a timing when the storage of the pulse data is started (i.e., the time of the beginning of the pulse data).

When a transmission timing comes (step S186: Yes), the CPU of the second vital signs information detecting sensor 20H reads out the pulse data and the second absolute time information from the storage section 23B, and transmits the pulse data and second absolute time information which are read out, to the receiver 30 through the wireless communicating section 26B (step S188). When the wireless communicating section 26B is set to a sleep state until the transmission timing comes, it is possible to save power consumption.

For example, the transmission timing is a timing when the pulse data stored in the storage section 23B exceed a threshold.

Alternatively, steps S184 and S186 may be omitted, and the pulse data of the patient 50 which are detected by the vital signs information detecting section 21B, and the like may be transmitted directly (without being stored in the storage section 23B) to the receiver 30.

The second vital signs information detecting sensor 20H then clears the pulse data storage section 23Ba (step S190). Namely, the stored contents of the pulse data storage section 23Ba are deleted.

Thereafter, the second vital signs information detecting sensor 20H repeatedly executes the processes of the steps S184 to S190.

When the electrocardiogram data and first absolute time information which are transmitted by the first vital signs information detecting sensor 20G are received (step S192), and the pulse data and second absolute time information which are transmitted by the second vital signs information detecting sensor 20H are received (step S194), the receiver 30 executes the vital signs information display process (step S196). The vital signs information display process is a process in which the receiver 30 causes the electrocardiogram data and the pulse data to be displayed on the display 31 in a synchronized state.

Figure 20:
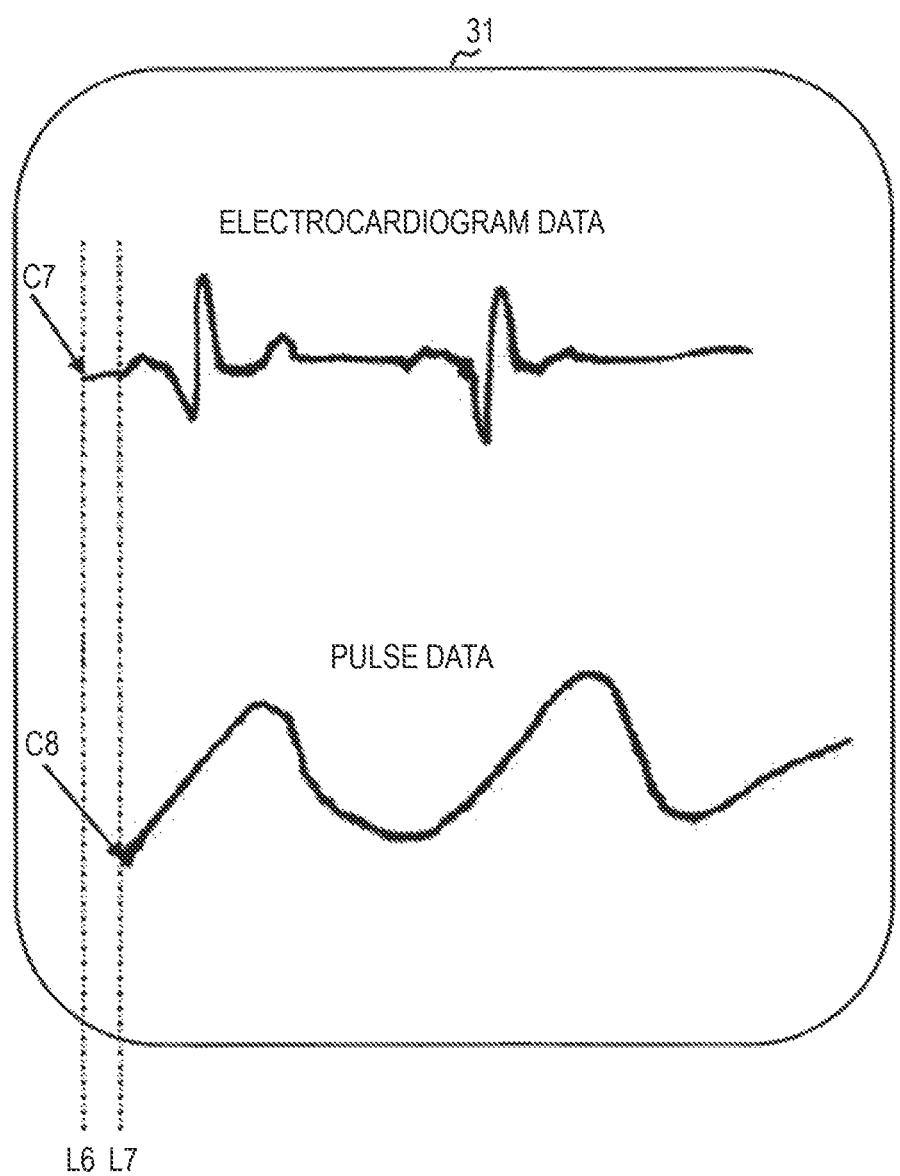
FIG. 20 illustrates display examples of the electrocardiogram data and the pulse data according to the fourth embodiment.

Specifically, the CPU of the receiver 30 causes the electrocardiogram data and the pulse data to be displayed on the display 31 so that a portion C7 (see FIG. 20) of the electrocardiogram data corresponding to the first time (the time indicated by the first absolute time information) is positioned on a line L6 indicating the first time, and a portion C8 (see FIG. 20) of the pulse data corresponding to the second time (the time indicated by the second absolute time information) is positioned on a line L7 indicating the second time. Namely, the electrocardiogram data and the pulse data are displayed on the display 31 in a synchronized state. The lines L6, L7 may be displayed on the display 31, or may not be displayed.

As described above, according to this embodiment, even when the first and second vital signs information detecting sensors 20G, 20H wirelessly transmit at different timings the sets of vital signs information (the electrocardiogram data and the pulse data) which are detected respectively by the sensors, the receiver 30 which is the receiving side of the vital signs information can treat the sets of vital signs information (the electrocardiogram data and the pulse data) as if they are detected respectively by the first and second vital signs information detecting sensors 20G 20H at the same time.

This is because, based on the first absolute time information which is received in the step S192, and the second absolute time information which is received in the step S194, the electrocardiogram data and the pulse data are displayed on the display 31 in a synchronized state.

Next, descriptions for modified examples will be presented.

In the above-described embodiments, a vital signs information detecting sensor which detects an electrocardiogram of the patient 50 is used as the first vital signs information detecting sensor 20A (20C, 20E, 20G), and a vital signs information detecting sensor which detects the pulse of the patient 50 is used as the second vital signs information detecting sensor 20B (20D, 20F, 20H). However, for example, a vital signs information detecting sensor which detects other vital signs information (for example, the body temperature of the patient 50) may be used as the first vital signs information detecting sensor 20A (20C, 20E, 20G), and a vital signs information detecting sensor which detects still other vital signs information (for example, the blood pressure of the patient 50) may be used as the second vital signs information detecting sensor 20B (20D, 20F, 20H).

In the above-described embodiments, two vital signs information detecting sensors (the first vital signs information detecting sensor 20A (20C, 20E, 20G) and the second vital signs information detecting sensor 20B (20D, 20F, 20H)) are used. However, for example, three or more vital signs information detecting sensors may be used.

In the above-described embodiments, a communication module (e.g., a BLE module) compatible to the BLE (Bluetooth Low Energy) technology is used as the wireless communicating section 26A, 26B, or 35. However, for example, a communication module (e.g., a wireless LAN module) compatible to the wireless LAN technology may be used as the wireless communicating section 26A, 26B, or 35.

In the above-described first embodiment, an acceleration sensor (the first acceleration sensor 24A and the second acceleration sensor 24B) is used as the motion detecting section. However, for example, an angular velocity sensor or another sensor which can detect a motion of the patient 50 may be used as the motion detecting section.

All the numerical values indicated in the embodiments are exemplarily presented. As a matter of course, appropriate numerical values different from the values may be used.

According to an aspect of the present disclosure, there is provided a vital signs information synchronization system comprising: a first vital signs information detecting sensor; a second vital signs information detecting sensor; and an information processing device, wherein the first vital signs information detecting sensor and the second vital signs information detecting sensor are configured to be attached on a living body; wherein the first vital signs information detecting sensor comprises: a first vital signs information detecting section configured to detect over time first vital signs information of the living body; a first motion detecting section configured to detect over time first motion information of the living body; and a first transmitting section configured to transmit to the information processing device the first vital signs information detected by the first vital signs information detecting section and the first motion information detected by the first motion detecting section; wherein the second vital signs information detecting sensor comprises: a second vital signs information detecting section configured to detect over time second vital signs information of the living body; a second motion detecting section configured to detect over time second motion information of the living body; and a second transmitting section configured to transmit to the information processing device the second vital signs information detected by the second vital signs information detecting section and the second motion information detected by the second motion detecting section; and wherein the information processing device comprises: a receiving section configured to receive the first vital signs information and the first motion information transmitted by the first transmitting section as well as the second vital signs information and the second motion information transmitted by the second transmitting section; a display; and a display control section configured to cause the display to display the first vital signs information and the second vital signs information received by the receiving section in a synchronized state, on the basis of the first motion information and the second motion information received by the receiving section.

The first vital signs information detecting sensor may comprise: a first vital signs information storage section configured to store the first vital signs information detected by the first vital signs information detecting section; and a first motion information storage section configured to store the first motion information detected by the first motion detecting section; the second vital signs information detecting sensor may comprise: a second vital signs information storage section configured to store the second vital signs information detected by the second vital signs information detecting section; and a second motion information storage section configured to store the second motion information detected by the second motion detecting section; the first transmitting section may be configured to transmit the first vital signs information stored in the first vital signs information storage section and the first motion information stored in the first motion information storage section to the information processing device at a prescribed timing; and the second transmitting section may be configured to transmit the second vital signs information stored in the second vital signs information storage section and the second motion information stored in the second motion information storage section to the information processing device at a prescribed timing.

The first motion detecting section may be a first acceleration sensor configured to detect over time first acceleration information of the living body; the second motion detecting section may be a second acceleration sensor configured to detect over time second acceleration information of the living body; the first motion information may be the first acceleration information detected by the first acceleration sensor; and the second motion information may be the second acceleration information detected by the second acceleration sensor.

According to an aspect of the present disclosure, there is also provided a vital signs information synchronization system comprising: a first vital signs information detecting sensor; a second vital signs information detecting sensor; and an information processing device, wherein the first vital signs information detecting sensor and the second vital signs information detecting sensor are configured to be attached on a living body; wherein the first vital signs information detecting sensor comprises: a first vital signs information detecting section configured to detect over time first vital signs information of the living body; a first receiving section configured to receive first absolute time information transmitted by the information processing device; a first counter configured to start a count-up operation in a case where the first receiving section receives the first absolute time information; and a first transmitting section configured to transmit to the information processing device the first vital signs information detected by the first vital signs information detecting section, the first absolute time information received by the first receiving section, and first count information indicative of a value counted by the first counter; wherein the second vital signs information detecting sensor comprises: a second vital signs information detecting section configured to detect over time second vital signs information of the living body; a second receiving section configured to receive second absolute time information transmitted by the information processing device; a second counter configured to start a count-up operation in a case where the second receiving section receives the second absolute time information; and a second transmitting section configured to transmit to the information processing device the second vital signs information detected by the second vital signs information detecting section, the second absolute time information received by the second receiving section, and second count information indicative of a value counted by the second counter; and wherein the information processing device comprises: a third receiving section configured to receive the first vital signs information, the first absolute time information and the first count information transmitted by the first transmitting section as well as the second vital signs information, the second absolute time information and the second count information transmitted by the second transmitting section; a display; and a display control section configured to cause the display to display the first vital signs information and the second vital signs information received by the third receiving section in a synchronized state, on the basis of the first absolute time information, the first count information, the second absolute time information and the second count information received by the third receiving section.

The first vital signs information detecting sensor may comprise a first vital signs information storage section configured to store the first vital signs information detected by the first vital signs information detecting section; the second vital signs information detecting sensor may comprise a second vital signs information storage section configured to store the second vital signs information detected by the second vital signs information detecting section; the first transmitting section may be configured to transmit the first vital signs information stored in the first vital signs information storage section, the first absolute time information received by the first receiving section and the first count information obtained by the first counter to the information processing device at a prescribed timing; and the second transmitting section may be configured to transmit the second vital signs information stored in the second vital signs information storage section, the second absolute time information received by the second receiving section and the second count information obtained by the second counter to the information processing device at a prescribed timing.

The timing may be so prescribed as to cause an difference between the first vital signs information and the second vital signs information which are displayed on the display to fall within an allowable range.

The first transmitting section may be configured to transmit, in place of the first absolute time information and the first count information, a first time calculated on the basis of the first absolute time information and the first count information; and the second transmitting section may be configured to transmit, in place of the second absolute time information and the second count information, a second time calculated on the basis of the second absolute time information and the second count information.

According to an aspect of the present disclosure, there is also provided a vital signs information synchronization system comprising: a first vital signs information detecting sensor; a second vital signs information detecting sensor; and an information processing device, wherein the first vital signs information detecting sensor and the second vital signs information detecting sensor are configured to be attached on a living body; wherein the first vital signs information detecting sensor comprises: a first vital signs information detecting section configured to detect over time first vital signs information of the living body; a first receiving section configured to receive first absolute time information transmitted by the information processing device; a first clock section configured to start a time count operation from time indicated by the first absolute time information received by the first receiving section; and a first transmitting section configured to transmit the first vital signs information detected by the first vital signs information detecting section and first time information indicative of a value counted by the first clock section to the information processing device; wherein the second vital signs information detecting sensor comprises: a second vital signs information detecting section configured to detect over time second vital signs information of the living body; a second receiving section configured to receive second absolute time information transmitted by the information processing device; a second clock section configured to start a time count operation from time indicated by the second absolute time information received by the second receiving section; and a second transmitting section configured to transmit the second vital signs information detected by the second vital signs information detecting section and second time information indicative of a value counted by the second clock section to the information processing device; and wherein the information processing device comprises: a third receiving section configured to receive the first vital signs information and the first time information transmitted by the first transmitting section as well as the second vital signs information and the second time information transmitted by the second transmitting section; a display; and a display control section configured to cause the display to display the first vital signs information and the second vital signs information received by the third receiving section in a synchronized state, on the basis of the first time information and the second time information received by the third receiving section.

According to an aspect of the present disclosure, there is also provided a vital signs information synchronization system comprising: a first vital signs information detecting sensor; a second vital signs information detecting sensor; and an information processing device, wherein the first vital signs information detecting sensor and the second vital signs information detecting sensor are configured to be attached on a living body; wherein the first vital signs information detecting sensor comprises: a first receiving section configured to receive first absolute time information transmitted by the information processing device; a first vital signs information detecting section configured to detect over time first vital signs information of the living body in a case where the first receiving section receives the first absolute time information; and a first transmitting section configured to transmit the first vital signs information detected by the first vital signs information detecting section and the first absolute time information received by the first receiving section to the information processing device; wherein the second vital signs information detecting sensor comprises: a second receiving section configured to receive second absolute time information transmitted by the information processing device; a second vital signs information detecting section configured to detect over time second vital signs information of the living body in a case where the second receiving section receives the second absolute time information; and a second transmitting section configured to transmit the second vital signs information detected by the second vital signs information detecting section and the second absolute time information received by the second receiving section to the information processing device; and wherein the information processing device comprises: a third receiving section configured to receive the first vital signs information and the first absolute time information transmitted by the first transmitting section as well as the second vital signs information and the second absolute time information transmitted by the second transmitting section; a display; and a display control section configured to cause the display to display the first vital signs information and the second vital signs information received by the third receiving section in a synchronized state, on the basis of the first absolute time information and the second absolute time information received by the third receiving section.

According to an aspect of the present disclosure, there is also provided a vital signs information synchronization method comprising: attaching a first vital signs information detecting sensor and a second vital signs information detecting sensor to a living body; detecting over time first vital signs information and first motion information of the living body by the first vital signs information detecting sensor; transmitting the first vital signs information and the first motion information from the first vital signs information detecting sensor to an information processing device; detecting over time second vital signs information and second motion information of the living body by the second vital signs information detecting sensor; transmitting the second vital signs information and the second motion information from the second vital signs information detecting sensor to the information processing device; and displaying the first vital signs information and the second vital signs information on a display of the information processing device in a synchronized state, on the basis of the first motion information and the second motion information.

According to an aspect of the present disclosure, there is also provided a vital signs information synchronization method comprising: attaching a first vital signs information detecting sensor and a second vital signs information detecting sensor to a living body; detecting over time first vital signs information of the living body by the first vital signs information detecting sensor; receiving first absolute time information transmitted from an information processing device by the first vital signs information detecting sensor; starting a count-up operation to obtain first count information by the first vital signs information detecting sensor in response to the receiving of the first absolute time information; transmitting the first vital signs information, the first absolute time information, and the first count information from the first vital signs information detecting sensor to the information processing device; detecting over time second vital signs information of the living body by the second vital signs information detecting sensor; receiving second absolute time information transmitted from the information processing device by the second vital signs information detecting sensor; starting a count-up operation to obtain second count information by the second vital signs information detecting sensor in response to the receiving of the second absolute time information; transmitting the second vital signs information, the second absolute time information, and the second count information from the second vital signs information detecting sensor to the information processing device; and displaying the first vital signs information and the second vital signs information on a display of the information processing device in a synchronized state, on the basis of the first absolute time information, the first count information, the second absolute time information, and the second count information.

According to an aspect of the present disclosure, there is also provided a vital signs information synchronization method comprising: attaching a first vital signs information detecting sensor and a second vital signs information detecting sensor to a living body; detecting over time first vital signs information of the living body by the first vital signs information detecting sensor; receiving first absolute time information transmitted from an information processing device by the first vital signs information detecting sensor; starting a time count operation to obtain first time information by the first vital signs information detecting sensor from time indicated by the first absolute time information; transmitting the first vital signs information and the first time information from the first vital signs information detecting sensor to the information processing device; detecting over time second vital signs information of the living body by the second vital signs information detecting sensor; receiving second absolute time information transmitted from the information processing device by the second vital signs information detecting sensor; starting a time count operation to obtain second time information by the second vital signs information detecting sensor from time indicated by the second absolute time information; transmitting the second vital signs information and the second time information from the second vital signs information detecting sensor to the information processing device; and displaying, the first vital signs information and the second vital signs information on a display of the information processing device in a synchronized state, on the basis of the first time information and the second time information.

According to an aspect of the present disclosure, there is also provided a vital signs information synchronization method comprising: attaching a first vital signs information detecting sensor and a second vital signs information detecting sensor to a living body; receiving first absolute time information transmitted from an information processing device by the first vital signs information detecting sensor; detecting over time first vital signs information of the living body by the first vital signs information detecting sensor in response to the receiving of the first absolute time information; transmitting the first vital signs information and the first absolute time information from the first vital signs information detecting sensor to the information processing device; receiving second absolute time information transmitted from the information processing device by the second vital signs information detecting sensor; detecting over time second vital signs information of the living body by the second vital signs information detecting sensor in response to the receiving of the second absolute time information; transmitting the second vital signs information and the second absolute time information from the second vital signs information detecting sensor to the information processing device; and displaying, the first vital signs information and the second vital signs information on a display of the information processing device in a synchronized state, on the basis of the first absolute time information and the second absolute time information.

According to an aspect of the present disclosure, there is also provided a vital signs information detecting sensor comprising: a vital signs information detecting section configured to detect over time vital signs information of living body; a motion detecting section configured to detect over time motion information of the living body; and a transmitting section configured to transmit the vital signs information detected by the vital signs information detecting section and the motion information detected by the motion detecting section to an external device.

According to an aspect of the present disclosure, there is also provided a vital signs information detecting sensor comprising: a vital signs information detecting section configured to detect over time vital signs information of living body; a receiving section configured to receive absolute time information transmitted by an external device; a counter configured to start a count-up operation to obtain count information in a case where the receiving section receives the absolute time information; and a transmitting section configured to transmit to the external device the vital signs information detected by the vital signs information detecting section, the absolute time information received by the receiving section, and the count information obtained by the counter.

According to an aspect of the present disclosure, there is also provided a vital signs information detecting sensor comprising: a vital signs information detecting section configured to detect over time vital signs information of living body; a receiving section configured to receive absolute time information transmitted by an external device; a clock section configured to start a time count operation from time indicated by the absolute time information to obtain time information; and a transmitting section configured to transmit the vital signs information detected by the vital signs information detecting section and the time information obtained by the counter to the external device.

According to an aspect of the present disclosure, there is also provided a vital signs information detecting sensor comprising: a receiving section configured to receive absolute time information transmitted by an external device; a vital signs information detecting section configured to detect over time vital signs information of living body in a case where the receiving section receives the absolute time information; and a transmitting section configured to transmit to the external device the vital signs information detected by the vital signs information detecting section and the absolute time information received by the receiving section.

What is claimed is:

1. A vital signs information synchronization system comprising:
    a first vital signs information detecting sensor;
    a second vital signs information detecting sensor; and
    an information processing device,
    wherein the first vital signs information detecting sensor and the second vital signs information detecting sensor are configured to be attached on a living body;
    wherein the first vital signs information detecting sensor comprises a first processor having a plurality of sections including:
        a first vital signs information detecting section configured to detect over time first vital signs information of the living body;
        a first motion detecting section configured to detect over time first motion information of the living body; and
        a first transmitting section configured to transmit to the information processing device the first vital signs information detected by the first vital signs information detecting section and the first motion information detected by the first motion detecting section;
    wherein the second vital signs information detecting sensor comprises a second processor having a plurality of sections including:
        a second vital signs information detecting section configured to detect over time second vital signs information of the living body;
        a second motion detecting section configured to detect over time second motion information of the living body; and
        a second transmitting section configured to transmit to the information processing device the second vital signs information detected by the second vital signs information detecting section and the second motion information detected by the second motion detecting section; and
    wherein the information processing device comprises:
        a receiver configured to receive the first vital signs information and the first motion information transmitted by the first transmitting section as well as the second vital signs information and the second motion information transmitted by the second transmitting section;
        a display; and
        a display controller configured to cause the display to display the first vital signs information and the second vital signs information received by the receiver in a synchronized state, on the basis of the first motion information and the second motion information received by the receiver.

2. The vital signs information synchronization system according to claim 1,
    wherein the first vital signs information detecting sensor further comprises:
        a first vital signs information storage configured to store the first vital signs information detected by the first vital signs information detecting section; and
        a first motion information storage configured to store the first motion information detected by the first motion detecting section;
    wherein the second vital signs information detecting sensor further comprises:
        a second vital signs information storage configured to store the second vital signs information detected by the second vital signs information detecting section; and
        a second motion information storage configured to store the second motion information detected by the second motion detecting section;
    wherein the first transmitting section is configured to transmit the first vital signs information stored in the first vital signs information storage and the first motion information stored in the first motion information storage to the information processing device at a prescribed timing; and wherein the second transmitting section is configured to transmit the second vital signs information stored in the second vital signs information storage and the second motion information stored in the second motion information storage to the information processing device at a prescribed timing.

3. The vital signs information synchronization system according to claim 1, wherein the first motion detecting section is a first acceleration sensor configured to detect over time first acceleration information of the living body;

wherein the second motion detecting section is a second acceleration sensor configured to detect over time second acceleration information of the living body;

wherein the first motion information is the first acceleration information detected by the first acceleration sensor; and wherein the second motion information is the second acceleration information detected by the second acceleration sensor.

\* \* \* \* \*